(12) United States Patent
Wellstein

(10) Patent No.: US 9,789,160 B2
(45) Date of Patent: Oct. 17, 2017

(54) TREATMENTS FOR LOWERING GLUCOSE LEVELS USING FGF BINDING PROTEIN 3

(71) Applicant: Georgetown University, Washington, DC (US)

(72) Inventor: Anton Wellstein, Washington, DC (US)

(73) Assignee: Georgetown University, Washington, DC (US)

(*) Notice: Subject to any disclaimer, the term of this patent is extended or adjusted under 35 U.S.C. 154(b) by 0 days.

(21) Appl. No.: 14/853,482

(22) Filed: Sep. 14, 2015

(65) Prior Publication Data

US 2016/0000861 A1    Jan. 7, 2016

Related U.S. Application Data

(63) Continuation-in-part of application No. PCT/US2014/026937, filed on Mar. 14, 2014, and a continuation-in-part of application No. PCT/US2014/026938, filed on Mar. 14, 2014.

(60) Provisional application No. 61/782,382, filed on Mar. 14, 2013, provisional application No. 61/782,347, filed on Mar. 14, 2013.

(51) Int. Cl.
    *A61K 38/16*    (2006.01)
    *A61K 38/17*    (2006.01)

(52) U.S. Cl.
    CPC ................. *A61K 38/1709* (2013.01)

(58) Field of Classification Search
    None
    See application file for complete search history.

(56) References Cited

U.S. PATENT DOCUMENTS

2002/0155543 A1    10/2002    Adams et al.
2009/0197256 A1    8/2009    Goppelt et al.
2009/0214513 A1    8/2009    Zhong et al.

FOREIGN PATENT DOCUMENTS

WO    2010/065439 A1    6/2010

OTHER PUBLICATIONS

Korner et al. N. Engl. J. Med. 349(10): 926-928, 2003.*
Science. 280: 1363-1387, 1998.*
Kanasaki et al. J. Biomed. Biotech. vol. 2011, Article ID 197636, 11 pages, 2011.*
Lutz et al. Ourr. Protoc. Pharmacol. Chapter: Unit 5.61, 2012.*
Zhang et al. J. Biol. Chem. 283(42): 28329-28337, 2008.*
Beenken et al. Nat. Rev. Drug Discov. 8(3): 235-253, 2009.*
Beenken et al. (2009) The FGF Family: Biology, Pathophysiology and Therapy, Nat. Rev. Drug Discov. 8:235-253.
Kir et al. (2011) FGF19 as a Postprandial, Insulin-Independent Activator of Hepatic Protein and Glycogen Synthesis, Science, 331:1621-1624.
Yamanaka et al. (2011) Inactivation of Fibroblast Growth Factor Binding Protein 3 Causes Anxiety Related Behaviors, Mol. Cell Neurosci. 46:200-212.
Zhang et al. (2008) Effect of FGF-Binding Protein 3 on Vascular Permeability, J. Biol. Chem, 283:28329-28337.

* cited by examiner

*Primary Examiner* — Christine J Saoud
(74) *Attorney, Agent, or Firm* — Morgan, Lewis & Bockius LLP

(57) ABSTRACT

The invention relates to methods of lowering blood glucose levels in a subject, with the methods comprising administering fibroblast growth factor binding protein 3 (FGFBP3) or a variant thereof to a subject in need of having lower glucose levels.

15 Claims, 13 Drawing Sheets

A

B

C

TREATMENTS FOR LOWERING GLUCOSE LEVELS USING FGF BINDING PROTEIN 3

STATEMENT REGARDING FEDERALLY SPONSORED RESEARCH OR DEVELOPMENT

Part of the work performed during development of this invention utilized U.S. Government funds through National Institutes of Health Grant Nos. RO1 CA71508 and PO1 HL068686. The U.S. Government has certain rights in this invention.

SEQUENCE LISTING INFORMATION

A computer readable text file, entitled "036681-5022-WO-SequenceListing.txt," created on or about 13 Mar. 2014 with a file size of about 9 kb contains the sequence listing for this application and is hereby incorporated by reference in its entirety.

BACKGROUND OF THE INVENTION

Field of the Invention

The invention relates to methods of treating a metabolic disorder in a subject, the method comprising administering fibroblast growth factor binding protein 3 (FGFBP3) to a subject in need of treatment of a metabolic disorder.

The invention also relates to methods of treating a metabolic disorder in a subject, the method comprising administering a complex of fibroblast growth factor 19 (FGF19), fibroblast growth factor 21 (FGF21) or fibroblast growth factor 23 (FGF23), plus fibroblast growth factor binding protein 3 (FGFBP3) to a subject in need of treatment of a metabolic disorder.

Background of the Invention

Fibroblast growth factor 19 (FGF19) and other members of the FGF19 family (i.e. FGF21 and FGF23, the so-called "endocrine FGFs") are involved in the regulation of metabolism. FGF19 and FGF21 have also been recently described as a sensitizer to insulin. In addition, some members of the FGF19 family interact with the co-receptor klotho to affect metabolism.

Previous studies indicate that FGF-binding proteins (FGFBP) can enhance the effects of FGF by mobilizing FGFs from their storage depots found in extracellular glycosaminoglycans or heparansulfate proteoglycans. In contrast to most other FGFs, members of the FGF19 family of proteins, i.e., FGF19, FGF21 and FGF23, show only very little binding to glycosaminoglycans or heparansulfates in the extracellular matrix. The most recently discovered member of the FGFBP3 family also appears to mobilize FGFs from such storage depots and bind to FGFs including FGF19 family members.

SUMMARY OF THE INVENTION

The invention relates to methods of treating a metabolic disorder in a subject, the method comprising administering fibroblast growth factor binding protein 3 (FGFBP3) to a subject in need of treatment of a metabolic disorder.

The invention also relates to methods of lowering blood glucose levels in a subject, the method comprising administering FGFBP3 to a subject in need of lowering of blood glucose levels.

The invention also relates to methods of lowering a subject's body weight, the method comprising administering FGFBP3 to a subject that is in need of lowering its body weight.

The invention also relates to methods of lowering a subject's atherogenic serum lipids, the method comprising administering FGFBP3 to a subject that is in need of lowering atherogenic lipids.

The invention also relates to methods of treating a metabolic disorder in a subject, the method comprising administering a complex of fibroblast growth factor 19 (FGF19), fibroblast growth factor 21 (FGF21) or fibroblast growth factor 23 (FGF23), plus fibroblast growth factor binding protein 3 (FGFBP3) to a subject in need of treatment of a metabolic disorder.

The invention also relates to methods of lowering blood glucose levels in a subject, the method comprising administering a complex of FGF19, FGF21 or FGF23 and FGFBP3 to a subject in need of lowering of blood glucose levels.

The invention also relates to methods of lowering a subject's body weight, the method comprising administering a complex of FGF19, FGF21 or FGF23 and FGFBP3 to a subject that is in need of lowering its body weight.

BRIEF DESCRIPTION OF THE DRAWINGS

FIGS. 3A, 3B show the effect when the test was conducted two hours after treatment. FIG. 3C shows the effect when the test was performed 24 hours after treatment. Even 7 days of dosing of BP3 alone with a single daily dose of BP3 lacked an effect on the baseline blood glucose or on the IPGTT test (FIG. 3D).

DETAILED DESCRIPTION OF THE INVENTION

Figure 1:
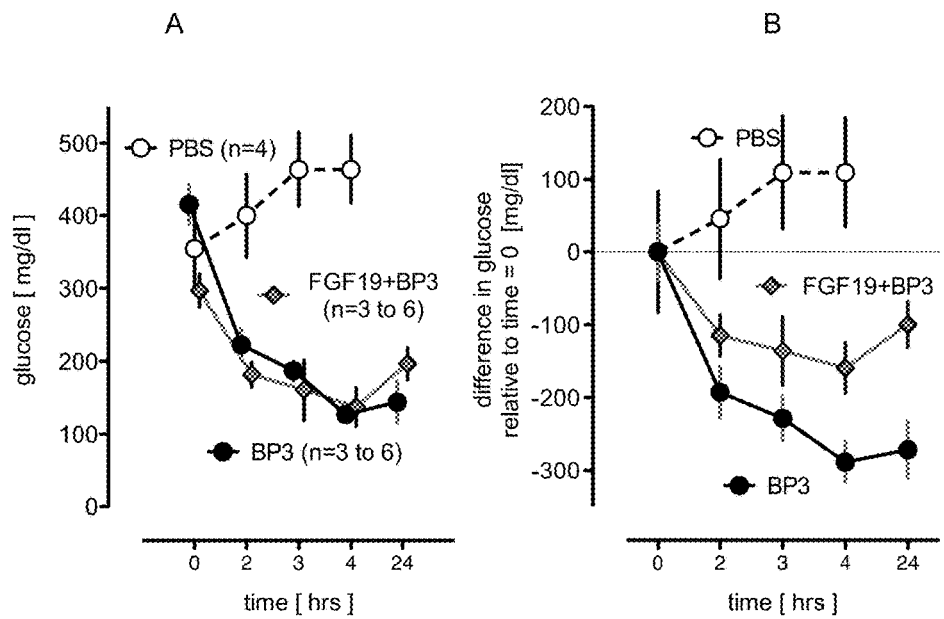
FIG. 1 depicts the effects of a single dose of FGFBP3 alone or FGF19+FGFBP3 treatments on glucose metabolism in fed ob/ob mice that are diabetic. The Left Panel, shows that upon intraperitoneal injection of FGFBP3 alone, glucose levels fell from a diabetic level to roughly normal levels (100 to 150 mg/dl) beginning within 2 hours after the first treatment. Levels stayed close to normal range (compared to controls) for 24 hours following injection. A comparison with an injection of FGF19+FGFBP3 (both panels), shows that FGFBP3 alone had the same absolute effect as the combination with FGF19. BP3 showed a greater relative effect (Right Panel) on lowering glucose levels when normalized to account for different baseline glucose levels.

The invention relates to methods of treating a metabolic disorder in a subject, the methods comprising administering a fibroblast growth factor binding protein 3 (FGFBP3) or an appropriate variant thereof to a subject in need of treatment of a metabolic disorder. The invention also relates to methods of treating a metabolic disorder in a subject, the methods comprising administering a complex of fibroblast growth factor 19 (FGF19), fibroblast growth factor 21 (FGF21) or fibroblast growth factor 23 (FGF23), plus fibroblast growth factor binding protein 3 (FGFBP3) or variant thereof to a subject in need of treatment of a metabolic disorder. As used herein, the term "subject" is used interchangeably with the term "patient" and is also used to include an animal, in particular a mammal, and even more particularly a non-human or human primate or dog or cat to give examples.

The fibroblast growth factor binding protein 3 (herein referred to interchangeably as BP3 or FGFBP3) is a secreted protein that binds to human FGF19, FGF21 and FGF23. Fibroblast growth factor 19 (FGF19) is the signature member of the FGF19 family of proteins that is involved in nutrient metabolism. The mouse ortholog to human FGF19 is known as FGF15 and is 218 amino acids in length, including the 25-amino acid signal sequence at the N-terminus. As used herein, "fibroblast growth factor 15" or "FGF15" or "mFGF15" is used to indicate any ortholog to hFGF19 and can include the full length amino acid sequence, with or without the N-terminus signal sequence. It is understood that a reference to "FGF19" or "hFGF19" herein will also include a reference to its art-accepted orthologs, such as mouse FGF15. In general the concentration of FGF19 (or mFGF15) is upregulated after feeding and binds preferentially to FGF Receptor 4 (FGFR4). Specifically, FGF19 is synthesized in the distal small intestine in response to uptake of bile acids via the nuclear bile receptor.

FGFBP3 is believed to act as a co-receptor with FGFR4. The full length amino acid sequence of human FGFBP3 is shown below as SEQ ID NO:1. The full length amino acid sequence of human FGFBP3, without the 26 amino-acid signal sequence, is shown below as SEQ ID NO:2. The C-terminus of FGFBP3 is shown below as SEQ ID NO:3.

As used herein, "FGFBP3" means a peptide that comprises the amino acid sequence of SEQ ID NO:3 or a variant thereof that still retains activity similar to the wild-type FGFBP3. Thus, the amino acid sequence of SEQ ID NOs:1 and 2 are just two embodiments of the term FGFBP3 as it is used herein. "Variants" of FGFBP3 are discussed below.

```
                                                              (SEQ ID NO: 1)
            MTPPKLRASL SPSLLLLLSG CLLAAARREK GAASNVAEPV PGPTGGSSGR FLSPEQHACS        60

WQLLLLPAPEA AAGSELALRC QSPDGARHQC AYRGHPERCA AYAARRAHFW KQVLGGLRKK       120

RRPCHDPAPL QARLCAGKKG HGAELRLVPR ASPPARPTVA GFAGESKPRA RNRGRTRERA        180

SGPAAGTPPP QSAPPKENPS ERKTNEGKRK AALVPNEERP MGTGPDPDGL DGNAELTETY        240

CAEKWHSLCN FFVNFWNG                                                    258

(SEQ ID NO: 2)
            RREK GAASNVAEPV PGPTGGSSGR FLSPEQHACS WQLLLPAPEA AAGSELALRC QSPDGARHQC    64

AYRGHPERCA AYAARRAHFW KQVLGGLRKK RRPCHDPAPL QARLCAGKKG HGAELRLVPR        124

ASPPARPTVA GFAGESKPRA RNRGRTRERA SGPAAGTPPP QSAPPKENPS ERKTNEGKRK        184

AALVPNEERP MGTGPDPDGL DGNAELTETY CAEKWHSLCN FFVNFWNG                     232

(SEQ ID NO: 3)
            LDGNAELTET YCAEKWHSLC NFFVNFWNG                                          29

(SEQ ID NO: 4)
            APPKENPSER KTNEGKRKAA LVPNEERPMG TGPDPDGLDG NAELTETYCA EKWHSLCNFF         60

VNFWNG                                                                   66
```

The present invention is directed to methods that include administration of FGFBP3. The FGFBP3 can, but need not, be specifically interacting with FGF19, i.e., specifically binding to one another. Other functions of FGFBP3 include but are not limited to the ability to interact with other members of the family of FGF19 proteins such as FGF21 and FGF23. FGFBP3 may exert its effect by interacting with FGF21 and/or FGF23.

The present invention is also directed to methods that include administration of a complex of FGF19 and FGFBP3. As used herein, the term "complex" as it relates to FGF19 and FGFBP3 means the presence of both FGFBP3 and FGF19. The FGF19 and FGFBP3 can, but need not, specifically interact, i.e., specifically bind to one another. In one embodiment, the FGF19 and FGFBP3 within the complex are specifically bound to one another. In another embodiment, the FGF19 and FGFBP3 within the complex are not necessarily specifically binding to one another.

Accordingly, in some embodiment of the methods of the present invention, full length FGFBP3 (a peptide amino acid sequence of SEQ ID NO:1) is administered. In select of these embodiments, the FGFBP3 comprises a peptide with an amino acid sequence that is 100% identical to the amino acid sequence of SEQ ID NO:1. In additional embodiments, the FGFBP3 consists of a peptide with an amino acid sequence that is 100% identical to the amino acid sequence of SEQ ID NO:1.

In other embodiments, full length FGFBP3 (a peptide amino acid sequence of SEQ ID NO:1) is complexed with FGF19. In select of these embodiments, the FGFBP3 in the complex comprises a peptide with an amino acid sequence that is 100% identical to the amino acid sequence of SEQ ID NO:1. In additional embodiments, the FGFBP3 in the complex consists of a peptide with an amino acid sequence that is 100% identical to the amino acid sequence of SEQ ID NO:1.

In additional embodiments of the methods of the present invention, full length FGFBP3 without the signal sequence (a peptide amino acid sequence of SEQ ID NO:2) is administered. In select of these embodiments, the FGFBP3 peptide comprises an amino acid sequence that is 100% identical to the amino acid sequence of SEQ ID NO:2. In additional embodiments, the FGFBP3 peptide consists of an amino acid sequence that is 100% identical to the amino acid sequence of SEQ ID NO:2.

In other embodiments, full length FGFBP3 without the signal sequence (a peptide amino acid sequence of SEQ ID NO:2) is complexed with FGF19. In select of these embodiments, the FGFBP3 in the complex comprises a peptide with an amino acid sequence that is 100% identical to the amino acid sequence of SEQ ID NO:2. In additional embodiments, the FGFBP3 in the complex consists of a peptide with an amino acid sequence that is 100% identical to the amino acid sequence of SEQ ID NO:2.

In still additional embodiment of the methods of the present invention, the C-terminal FGFBP3 (a peptide amino acid sequence of SEQ ID NO:3) is administered. In select of these embodiments, the FGFBP3 peptide comprises an amino acid sequence that is 100% identical to the amino acid sequence of SEQ ID NO:3. In additional embodiments, the FGFBP3 peptide consists of an amino acid sequence that is 100% identical to the amino acid sequence of SEQ ID NO:3.

In still additional embodiment of the methods of the present invention, the C-terminal FGFBP3 (a peptide amino acid sequence of SEQ ID NO:3) is complexed with FGF19. In select of these embodiments, the FGFBP3 in the complex comprises a peptide with an amino acid sequence that is 100% identical to the amino acid sequence of SEQ ID NO:3. In additional embodiments, the FGFBP3 in the complex consists of a peptide with an amino acid sequence that is 100% identical to the amino acid sequence of SEQ ID NO:3.

In still additional embodiment of the methods of the present invention, the C-terminal FGFBP3 "C66" peptide (a peptide amino acid sequence of SEQ ID NO:4) is administered. In select of these embodiments, the FGFBP3 peptide comprises an amino acid sequence that is 100% identical to the amino acid sequence of SEQ ID NO:4. In additional embodiments, the FGFBP3 peptide consists of an amino acid sequence that is 100% identical to the amino acid sequence of SEQ ID NO:4.

In still additional embodiment of the methods of the present invention, the C-terminal FGFBP3 "C66" peptide (a peptide amino acid sequence of SEQ ID NO:4) is complexed with FGF19. In select of these embodiments, the FGFBP3 in the complex comprises a peptide with an amino acid sequence that is 100% identical to the amino acid sequence of SEQ ID NO:4. In additional embodiments, the FGFBP3 in the complex consists of a peptide with an amino acid sequence that is 100% identical to the amino acid sequence of SEQ ID NO:4.

The terms "peptide," "polypeptide" and "protein" are used interchangeably herein. As used herein, an "isolated polypeptide" is intended to mean a polypeptide that has been completely or partially removed from its native environment. For example, polypeptides that have been removed or purified from cells are considered isolated. In addition, recombinantly produced polypeptides molecules contained in host cells are considered isolated for the purposes of the present invention. Moreover, a peptide that is found in a cell, tissue or matrix in which it is not normally expressed or found is also considered as "isolated" for the purposes of the present invention. Similarly, polypeptides that have been synthesized are considered to be isolated polypeptides. "Purified," on the other hand is well understood in the art and generally means that the peptides are substantially free of cellular material, cellular components, chemical precursors or other chemicals beyond, perhaps, buffer or solvent. "Substantially free" is not intended to mean that other components beyond the novel peptides are undetectable.

The invention also relates to the use of variants of FGFBP3 that still retain their ability to specifically interact, at least partially, with FGF19. In one embodiment, FGFBP3 variants comprise an amino acid sequence that is at least 75%, 80%, 85%, 86%, 87%, 88%, 89%, 90%, 91%, 92%, 93%, 94%, 95%, 96%, 97%, 98% or 99% identical to the amino acid sequences of SEQ ID NO: 3. In another embodiment, the FGFBP3 variant consists of a peptide with an amino acid sequence that is at least 75%, 80%, 85%, 86%, 87%, 88%, 89%, 90%, 91%, 92%, 93%, 94%, 95%, 96%, 97%, 98% or 99% identical to the amino acid sequences of SEQ ID NO: 3.

In one embodiment, FGFBP3 variants comprise an amino acid sequence that is at least 75%, 80%, 85%, 86%, 87%, 88%, 89%, 90%, 91%, 92%, 93%, 94%, 95%, 96%, 97%, 98% or 99% identical to the amino acid sequences of SEQ ID NO: 4. In another embodiment, the FGFBP3 variant consists of a peptide with an amino acid sequence that is at least 75%, 80%, 85%, 86%, 87%, 88%, 89%, 90%, 91%, 92%, 93%, 94%, 95%, 96%, 97%, 98% or 99% identical to the amino acid sequences of SEQ ID NO: 4.

In one embodiment, FGFBP3 variants comprise an amino acid sequence that is at least 75%, 80%, 85%, 86%, 87%, 88%, 89%, 90%, 91%, 92%, 93%, 94%, 95%, 96%, 97%, 98% or 99% identical to the amino acid sequences of SEQ ID NO: 1. In another embodiment, the FGFBP3 variant consists of a peptide with an amino acid sequence that is at least 75%, 80%, 85%, 86%, 87%, 88%, 89%, 90%, 91%, 92%, 93%, 94%, 95%, 96%, 97%, 98% or 99% identical to the amino acid sequences of SEQ ID NO: 1.

In one embodiment, FGFBP3 variants comprise an amino acid sequence that is at least 75%, 80%, 85%, 86%, 87%, 88%, 89%, 90%, 91%, 92%, 93%, 94%, 95%, 96%, 97%, 98% or 99% identical to the amino acid sequences of SEQ ID NO: 2. In another embodiment, the FGFBP3 variant consists of a peptide with an amino acid sequence that is at least 75%, 80%, 85%, 86%, 87%, 88%, 89%, 90%, 91%, 92%, 93%, 94%, 95%, 96%, 97%, 98% or 99% identical to the amino acid sequences of SEQ ID NO: 2.

As used herein, a metabolic disorder can be any disorder associated with metabolism, and examples include but are not limited to, obesity, central obesity, insulin resistance, glucose intolerance, abnormal glycogen metabolism, type 2 diabetes, hyperlipidemia, hypoalbuminemia, hypertriglyceridemia, metabolic syndrome, syndrome X, a fatty liver, fatty liver disease, polycystic ovarian syndrome, and acanthosis nigricans. In one embodiment, the methods are directed towards treating at least one component of postprandial metabolism, such as, but not limited to hepatic glycogen synthesis, protein synthesis and clearance of plasma glucose.

The terms "trait" and "phenotype" are used interchangeably herein and refer to any visible, detectable or otherwise measurable property of an organism such as symptoms of or susceptibility to a disorder. Typically the terms "trait" or "phenotype" are used herein to refer to symptoms of a metabolic disorder, or a susceptibility to an metabolic disorder. Examples of traits of metabolic disorders include but are not limited to high total cholesterol, low high-density lipoprotein (HDL) cholesterol, impaired fasting glucose levels, insulin resistance, hyperproinsulinemia, central obesity, elevated triglyceride levels, postprandial glucose levels, elevated uric acid levels, thyroid dysfunction, increased body-mass index (BMI), hypertension, impaired glucose tolerance, alterations in hormone and peptide levels (e.g., leptin, ghrelin, obstatin, adiponectin, perilipin, omentin), interactions with substances involved in insulin signaling, lipid, amino acid and glucose metabolism, life expectancy, increased systemic inflammatory state (e.g., as reflected in levels of C-reactive protein, interleukin-6, and TNF-alpha), depression, and sleep disordered breathing.

In additional embodiments, the peptide variants described herein are functional and capable of altering a subject's response in a glucose tolerance test when administered alone or in complex with FGF19. In some embodiments, the FGFBP3 variants of the present invention, alone or in complex with FGF19, have enhanced ability to alter a subject's response in a glucose tolerance test compared to wild-type FGFBP3. In some embodiments, the FGFBP3 variants of the present invention also have enhanced stability compared to the wild-type FGFBP3 regardless of their association with FGF19.

A polypeptide having an amino acid sequence at least, for example, about 95% "identical" to a reference an amino acid sequence, e.g., SEQ ID NO: 1, is understood to mean that the amino acid sequence of the polypeptide is identical to the reference sequence except that the amino acid sequence may include up to about five modifications per each 100 amino acids of the reference amino acid sequence. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using well known techniques. While there are several methods to measure identity between two polynucleotide or polypeptide sequences, the term "identity" is well known to skilled artisans (Carillo (1988) J. Applied Math. 48, 1073). Examples of computer program methods to determine identity and similarity between two sequences include, but are not limited to, GCG program package (Devereux (1984) Nucleic Acids Research 12, 387), BLASTP, ExPASy, BLASTN, FASTA (Atschul (1990) J. Mol. Biol. 215, 403) and FASTDB. Examples of methods to determine identity and similarity are discussed in Michaels (2011) Current Protocols in Protein Science, Vol. 1, John Wiley & Sons.

In one embodiment of the present invention, the algorithm used to determine identity between two or more polypeptides is BLASTP. In another embodiment of the present invention, the algorithm used to determine identity between two or more polypeptides is FASTDB, which is based upon the algorithm of Brutlag (1990) Comp. App. Biosci. 6, 237-245). In a FASTDB sequence alignment, the query and reference sequences are amino sequences. The result of sequence alignment is in percent identity. In one embodiment, parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the reference sequence is shorter or longer than the query sequence because of N-terminus or C-terminus additions or deletions, but not because of internal additions or deletions, a manual correction can be made, because the FASTDB program does not account for N-terminus and C-terminus truncations or additions of the reference sequence when calculating percent identity. For query sequences truncated at the N- or C-termini, relative to the reference sequence, the percent identity is corrected by calculating the number of residues of the query sequence that are N- and C-terminus to the reference sequence that are not matched/aligned, as a percent of the total bases of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the reference sequence that extend past the N- or C-termini of the query sequence may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue query sequence is aligned with a 100 residue reference sequence to determine percent identity. The deletion occurs at the N-terminus of the query sequence and therefore, the FASTDB alignment does not show a match/alignment of the first 10 residues at the N-terminus. The 10 unpaired residues represent 10% of the reference sequence (number of residues at the N- and C-termini not matched/total number of residues in the reference sequence) so 10% is subtracted from the percent identity score calculated by the FASTDB program. If the remaining 90 residues were perfectly matched (100% alignment) the final percent identity would be 90% (100% alignment—10% unmatched overhang). In another example, a 90 residue query sequence is compared with a 100 reference sequence, except that the deletions are internal deletions. In this case the percent identity calculated by FASTDB is not manually corrected, since there are no residues at the N- or C-termini of the subject sequence that are not matched/aligned with the query. In still another example, a 110 amino acid query sequence is aligned with a 100 residue reference sequence to determine percent identity. The addition in the query occurs at the N-terminus of the query sequence and therefore, the FASTDB alignment may not show a match/alignment of the first 10 residues at the N-terminus. If the remaining 100 amino acid residues of the query sequence have 95% identity to the entire length of the reference sequence, the N-terminal addition of the query would be ignored and the percent identity of the query to the reference sequence would be 95%.

As used herein, the terms "correspond(s) to" and "corresponding to," as they relate to sequence alignment, are intended to mean enumerated positions within the reference protein, e.g., wild-type FGFBP3, and those positions in the variant or ortholog of FGFBP3 that align with the positions with the reference protein. Thus, when the amino acid sequence of a subject FGFBP3 is aligned with the amino acid sequence of a reference FGFBP3, e.g., SEQ ID NO: 2, the amino acids in the subject sequence that "correspond to" certain enumerated positions of the reference sequence are those that align with these positions of the reference sequence, e.g., SEQ ID NO: 2, but are not necessarily in these exact numerical positions of the reference sequence. Methods for aligning sequences for determining corresponding amino acids between sequences are described herein.

The invention further embraces other species, preferably mammalian, homologs with amino acid sequences that correspond to FGFBP3. Species homologs, sometimes referred to as "orthologs," in general, share at least 35%, 40%, 45%, 50%, 60%, 65%, 70%, 75%, 80%, 85%, 90%, 95%, 96%, 97%, 98%, or 99% sequence identity with the human version of the full length binding proteins or the full length binding proteins without the signal sequence. Such corresponding sequences account for FGFBP3 from across a variety of species, such as canine, feline, mouse, rat, rabbit, monkey, etc.

FGFBP3 with an additional methionine residue at position −1 (Met$^{-1}$-peptide) are contemplated, as are variants with additional methionine and lysine residues at positions −2 and −1 (Met$^{-2}$-Lys$^{-1}$-peptide). Variants of FGFBP3 with additional Met, Met-Lys, or Lys residues (or one or more basic residues in general) are particularly useful for enhanced recombinant protein production in bacterial host cells.

Variants resulting from insertion of the polynucleotide encoding FGFBP3 into an expression vector system are also contemplated. For example, variants (usually insertions) may arise from when the amino terminus and/or the carboxy terminus of FGFBP3 is/are fused to another polypeptide.

In another aspect, the invention provides deletion variants wherein one or more amino acid residues in FGFBP3 are removed. Deletions can be effected at one or both termini of the FGFBP3, or with removal of one or more non-terminal amino acid residues of the FGFBP3. Deletion variants, therefore, include all fragments of the FGFBP3.

Within the confines of the disclosed percent identity, the invention also relates to substitution variants of disclosed polypeptides of the invention. Substitution variants include those polypeptides wherein one or more amino acid residues of FGFBP3 are removed and replaced with alternative residues. For example two variants of SEQ ID NOs: 1 or 2 are known to exist and the invention contemplates the use of these known variants in the methods described herein. Specifically, a variant of FGFBP3 wherein Alanine at position 107 of SEQ ID NO:1 is replaced with Threonine (A107T) is included in the methods of the present invention. Another variant of FGFBP3 wherein Glutamate at position 206 of SEQ ID NO:1 is replaced with Valine (E206V) is included in the methods of the present invention. Of course, positions 107 and 206 of SEQ ID NO:1 correspond to positions 81 and 180 of SEQ ID NO:2, and position 206 of SEQ ID NO:1 also corresponds to position 14 of SEQ ID NO:4. In one aspect, the substitutions are conservative in nature; however, the invention embraces substitutions that are also non-conservative. Conservative substitutions for this purpose may be defined as set out in the tables below. Amino acids can be classified according to physical properties and contribution to secondary and tertiary protein structure. A conservative substitution is recognized in the art as a substitution of one amino acid for another amino acid that has similar properties. Exemplary conservative substitutions are set out in below.

TABLE I

Conservative Substitutions

| Side Chain Characteristic | Amino Acid |
| --- | --- |
| Aliphatic | |
| Non-polar | Gly, Ala, Pro, Iso, Leu, Val |
| Polar-uncharged | Cys, Ser, Thr, Met, Asn, Gln |
| Polar-charged | Asp, Glu, Lys, Arg |
| Aromatic | His, Phe, Trp, Tyr |
| Other | Asn, Gln, Asp, Glu |

Alternatively, conservative amino acids can be grouped as described in Lehninger (1975) Biochemistry, Second Edition; Worth Publishers, pp. 71-77, as set forth below.

TABLE II

Conservative Substitutions

| Side Chain Characteristic | Amino Acid |
| --- | --- |
| Non-polar (hydrophobic) | |
| Aliphatic: | Ala, Leu, Iso, Val, Pro |
| Aromatic: | Phe, Trp |
| Sulfur-containing: | Met |
| Borderline: | Gly |
| Uncharged-polar | |
| Hydroxyl: | Ser, Thr, Tyr |
| Amides: | Asn, Gln |
| Sulfhydryl: | Cys |

TABLE II-continued

Conservative Substitutions

| Side Chain Characteristic | Amino Acid |
| --- | --- |
| Borderline: | Gly |
| Positively Charged (Basic): | Lys, Arg, His |
| Negatively Charged (Acidic): | Asp, Glu |

And still other alternative, exemplary conservative substitutions are set out below.

TABLE III

Conservative Substitutions

| Original Residue | Exemplary Substitution |
| --- | --- |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

It should be understood that the definition of peptides or polypeptides of the invention is intended to include polypeptides bearing modifications other than insertion, deletion, or substitution of amino acid residues. By way of example, the modifications may be covalent in nature, and include for example, chemical bonding with polymers, lipids, other organic and inorganic moieties. Such derivatives may be prepared to increase circulating half-life of a polypeptide, or may be designed to improve the targeting capacity of the polypeptide for desired cells, tissues or organs. Similarly, the invention further embraces FGFBP3 or variants thereof that have been covalently modified to include one or more water-soluble polymer attachments such as polyethylene glycol, polyoxyethylene glycol or polypropylene glycol.

Compositions in which the FGFBP3 or variants thereof is linked to a polymer are included within the scope of the present invention. The polymer may be water soluble to prevent precipitation of the protein in an aqueous environment, such as a physiological environment. Suitable water-soluble polymers may be selected from the group consisting of, for example, polyethylene glycol (PEG), monomethoxy-polyethylene glycol, dextran, cellulose, or other carbohydrate based polymers, poly-(N-vinyl pyrrolidone) polyethylene glycol, polypropylene glycol homopolymers, a polypropylene oxide/ethylene oxide copolymer polyoxyethylated polyols (e.g., glycerol) and polyvinyl alcohol. The selected polymer is usually modified to have a single reactive group, such as an active ester for acylation or an aldehyde for alkylation, so that the degree of polymerization may be controlled. Polymers may be of any molecular weight, and may be branched or unbranched, and mixtures of such polymers may also be used. When the chemically modified NgR polymer is destined for therapeutic use, pharmaceutically acceptable polymers will be selected for use.

Pegylation of FGFBP3 or variants thereof may be carried out by any of the pegylation reactions known in the art. In one method, the pegylation is carried out via an acylation reaction or an alkylation reaction with a reactive polyethylene glycol molecule (or an analogous reactive water-soluble polymer). A preferred water-soluble polymer for pegylation of polypeptides is polyethylene glycol (PEG), including, but not limited to bi-functional PEGs. As used herein, "polyethylene glycol" is meant to encompass any of the forms of PEG that have been used to derivatize other proteins, such as mono (Cl-ClO) alkoxy- or aryloxy-polyethylene glycol.

Chemical derivatization of FGFBP3 or variants thereof may be performed under any suitable conditions used to react a biologically active substance with an activated polymer molecule. Methods for preparing pegylated FGFBP3 or variants thereof will generally comprise the steps of (a) reacting the polypeptide with polyethylene glycol, such as a reactive ester or aldehyde derivative of PEG, under conditions whereby FGFBP3 or variants thereof becomes attached to one or more PEG groups, and (b) obtaining the reaction products. It will be apparent to one of ordinary skill in the art to select the optimal reaction conditions or the acylation reactions based on known parameters and the desired result.

Pegylated and other polymer-modified FGFBP3 or variants thereof may generally be used in the methods of the current invention. The chemically-derivatized polymer-modified FGFBP3 or variants thereof disclosed herein may have additional activities, enhanced or reduced biological activity, or other characteristics, such as increased or decreased half-life, as compared to the nonderivatized molecules. The modified FGFBP3 or variants thereof, alone or in complex, may be employed alone, together, or in combination with other pharmaceutical compositions. For example, cytokines, growth factors, antibiotics, anti-inflammatories and/or chemotherapeutic agents may be co-administered as is appropriate for the indication being treated.

The present invention provides compositions comprising purified polypeptides, alone or in complex, of the invention. Examples of compositions include but are not limited to a pharmaceutically acceptable, i.e., sterile and non-toxic, liquid, semisolid, or solid diluent that serves as a pharmaceutical vehicle, excipient or medium. Any diluent known in the art may be used. Exemplary diluents include, but are not limited to, water, saline solutions, polyoxyethylene sorbitan monolaurate, magnesium stearate, methyl- and propylhydroxybenzoate, talc, alginates, starches, lactose, sucrose, dextrose, sorbitol, mannitol, glycerol, calcium phosphate, mineral oil and cocoa butter.

In one embodiment, the invention provides fusion proteins comprising at least a first and a second fusion peptide. The fusion partners are, generally speaking, covalently bonded to one another via a typical amine bond between the fusion peptides, thus creating one contiguous amino acid chain. Types of fusion proteins provided by the present invention include but are not limited to, fusions with secretion signals and other heterologous functional regions. Thus, for instance, a region of additional amino acids, particularly charged amino acids, may be added to the N-terminus of the FGFBP3 or variant thereof to improve stability and persistence in the host cell, during purification or during subsequent handling and storage.

Additional fusion proteins include fusions for enhancing translocation of the protein across cell membranes. For example, Tat is an 86-amino acid protein involved in the replication of human immunodeficiency virus type 1 (HIV-1). The HIV-1 Tat transactivation protein is efficiently taken up by cells, and it has been demonstrated that low concentrations (nM) are sufficient to transactivate a reporter gene expressed from the HIV-1 promoter. Exogenous Tat protein is able to translocate through the plasma membrane and reach the nucleus to transactivate the viral genome. Tat peptide-mediated cellular uptake and nuclear translocation have been demonstrated in several systems. Chemically coupling a Tat-derived peptide (residues 37-72 of Tat) to several proteins results in their internalization in several cell lines or tissues (Fawell (1994) Proc. Natl. Acad. Sci. USA 91, 664-668.

It is well-known that a region of the Tat protein centered on a cluster of basic amino acids is responsible for this translocation activity. A synthetic peptide consisting of the Tat basic amino acids 48-60 with a cysteine residue at the C-terminus coupled to fluorescein maleimide translocates to the cell nucleus as determined by fluorescence microscopy. In addition, a fusion protein (Tat-NLS-β-Gal) consisting of Tat amino acids 48-59 fused by their amino-terminus to β-galactosidase amino acids 9-1023 translocates to the cell nucleus in an ATP-dependent, cytosolic factor-independent manner. Accordingly, the fusion proteins of the present invention may comprise all or a portion of HIV-Tat, such as any sequential residues of the Tat protein basic peptide motif 37-72 (37-CFITKALGISYGRKKRRQRRRPPQG-SQTHQVSLSKQ-72 (SEQ ID NO: 5). The minimum number of amino acid residues can be in the range of from about three to about six. In one embodiment, the Tat portion of the fusion protein is from about three to about five contiguous amino acids in length. In another embodiment, the Tat portion of the fusion protein is about four amino acids in length, i.e., the minimal requirement for one alpha helical turn. In another embodiment, the Tat portion of the fusion protein comprises Tat protein residues 48-57 (GRK-KRRQRRR) (SEQ ID NO: 6).

In additional embodiments of fusion proteins, a region may be added to facilitate purification. For example, "histidine tags" ("his tags") or "lysine tags" may be appended to the first fusion peptide. Examples of histidine tags include, but are not limited to hexaH, heptaH and hexaHN. Examples of lysine tags include, but are not limited to pentaL, heptaL and FLAG. Such regions may be removed prior to final preparation of the FGFBP3 or variant thereof. Other examples of a second fusion peptide include, but are not limited to, glutathione S-transferase (GST) and alkaline phosphatase (AP).

The addition of peptide moieties to proteins, whether to engender secretion or excretion, to improve stability and to facilitate purification or translocation, among others, is a familiar and routine technique in the art and may include modifying amino acids at the terminus to accommodate the tags. For example in SEQ ID NOs: 1, 2, 3 or 4, the N-terminus amino acid may be modified to, for example, arginine and/or serine to accommodate a tag. Of course, the amino acid residues of the C-terminus may also be modified to accommodate tags. One particularly useful fusion protein comprises a heterologous region from immunoglobulin that can be used solubilize proteins. For example, EP A0464 533 discloses fusion proteins comprising various portions of constant region of immunoglobin molecules together with another human protein or part thereof. In many cases, the Fc part in a fusion protein is thoroughly advantageous for use in therapy and diagnosis and thereby results, for example, in improved pharmacokinetic properties (EP A0232 262). On the other hand, for some uses, it would be desirable to be able to delete the Fc part after the fusion protein has been expressed, detected and purified in the advantageous manner described.

The fusion proteins of the current invention can be recovered and purified from recombinant cell cultures by well-known methods including, but not limited to, ammonium sulfate or ethanol precipitation, acid extraction, anion or cation exchange chromatography, phosphocellulose chromatography, hydrophobic interaction chromatography, affinity chromatography, e.g., immobilized metal affinity chromatography (IMAC), hydroxylapatite chromatography and lectin chromatography. High performance liquid chromatography ("HPLC") may also be employed for purification. Well-known techniques for refolding protein may be employed to regenerate active conformation when the fusion protein is denatured during isolation and/or purification.

Fusion proteins of the present invention include, but are not limited to, products of chemical synthetic procedures and products produced by recombinant techniques from a prokaryotic or eukaryotic host, including, for example, bacterial, yeast, higher plant, insect and mammalian cells. Depending upon the host employed in a recombinant production procedure, the fusion proteins of the present invention may be glycosylated or may be non-glycosylated. In addition, fusion proteins of the invention may also include an initial modified methionine residue, in some cases as a result of host-mediated processes.

The FGFBP3 or variant, alone or in complex, thereof can be prepared as a pharmaceutical composition. For example, one or more cofactors may also be added to the FGFBP3 or variant thereof, or to the complex of FGFBP3 or variant thereof and FGF19, to form a composition. Cofactors that may be added include, but are not limited to, heparin, hyaluronic acid, a fibronectin, an elastin, a laminin, albumin, a proteoglycan, collagen, gelatin, a divalent cation, calcium chloride, zinc sulfate, magnesium chloride, sodium bicarbonate, sodium chloride, sodium acetate, or sodium phosphate. In some embodiments, a protein or a protein fragment may be added as a cofactor to the FGFBP3 or variant thereof. In other embodiments, a protein or a protein fragment may be added as a cofactor to the complex of FGFBP3 or variant thereof and FGF19.

As used herein, "pharmaceutically acceptable carrier" or "pharmaceutical carrier" is intended to include any and all solvents, dispersion media, coatings, antibacterial and antifungal agents, isotonic and absorption delaying agents, and the like, compatible with pharmaceutical administration. The nature of the pharmaceutical carrier or other ingredients will depend on the specific route of administration and particular embodiment of the invention to be administered. Examples of techniques and protocols that are useful in this context are, inter alio, found in Remington: The Science and Practice of Pharmacy (2010), Lippincott Williams & Wilkins. Examples of such pharmaceutical carriers or diluents include, but are not limited to, water, saline, Ringer's solution, dextrose solution and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include oral and parenteral (e.g., intravenous, intradermal, subcutaneous, inhalation, transdermal (topical), transmucosal and rectal administration). Solutions or suspensions used for parenteral, intradermal or subcutaneous application can include, but are not limited to, a sterile diluent such as water for injection, saline solution, fixed oils, polyethylene glycols, glycerine, propylene glycol or other synthetic solvents, antibacterial agents such as benzyl alcohol or methyl parabens, antioxidants such as ascorbic acid or sodium bisulfite, chelating agents such as ethylenediaminetetraacetic acid, buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable pharmaceutical carriers include physiological saline, bacteriostatic water, Cremophor EL™ (BASF) or phosphate buffered saline (PBS). In all cases, the compositions must be sterile and should be fluid to the extent that easy syringeability exists. It must be stable under the conditions of manufacture and storage and must be preserved against the contaminating action of microorganisms such as bacteria and fungi. The pharmaceutical carrier can be a solvent or dispersion medium containing, for example, water, ethanol, polyol (for example, glycerol, propylene glycol and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it may be desirable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound/composition in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutical carrier. They can be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition. The tablets, pills, capsules, troches and the like may contain any of the following ingredients, or compounds of a similar nature, such as but not limited to a binder, such as microcrystalline cellulose, gum tragacanth or gelatin, an excipient such as starch or lactose, a disintegrating agent such as alginic acid, Primogel or corn starch, a lubricant such as magnesium stearate or Sterotes, a glidant such as colloidal silicon dioxide, a sweetening agent such as sucrose or saccharin, or a flavoring agent such as peppermint, methyl salicylate or flavoring.

In one embodiment, the active is prepared with pharmaceutical carriers that will protect the active against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These compositions can be prepared according to methods known to those skilled in the art, for example, as described in U.S. Pat. No. 4,522,811. It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of the active calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The pharmaceutical compositions can be included in a container, pack or dispenser together with instructions for administration.

The dosage of the FGFBP3 and/or the dosage of the FGFBP3-FGF19 complex will depend on the disorder or condition to be treated and other clinical factors such as weight and condition of the human or animal and the route of administration of the compound. For treating human or animals, the FGFBP3 or variant thereof, or the complex, can be administered at a dose of between about 0.005 mg/kg of body weight to 500 mg/kg of body weight. Therapy is typically administered at lower dosages and is continued until the desired therapeutic outcome is observed.

Methods of determining the dosages of composition to be administered to a patient and modes of administering compositions to an organism are disclosed in, for example, WO 96/22976. Those skilled in the art will appreciate that such descriptions are applicable to the present invention and can be easily adapted to it.

The proper dosage depends on various factors such as the type of disorder being treated, the particular composition being used and the size and physiological condition of the patient. Therapeutically effective doses for the compositions described herein can be estimated initially from cell culture and animal models. For example, a dose can be formulated in animal models to achieve a circulating concentration range that initially takes into account the $IC_{50}$ as determined in cell culture assays. The animal model data can be used to more accurately determine useful doses in humans.

The invention also relates to methods of altering intracellular signaling of a cell, comprising contacting cells with FGFBP3 or a variant thereof, or comprising contacting cells with the complex of FGFBP3 or a variant thereof plus FGF19, wherein the cell possesses a receptor that specifically binds to or associates with FGFBP3. In one embodiment, the receptor is the fibroblast growth factor receptor 4 (FGFR4). The specific binding of the FGFBP3 or the complex to a receptor will, in turn, initiate the intracellular signaling cascade that is normally associated with FGFBP3. For example, FIG. 12 demonstrates that administration of the complex of FGFBP3 or a variant thereof and FGF19 results in phosphorylation of Erk1/2. Accordingly, the present invention provides for methods of stimulating phosphorylation of Erk1/2 in a cell comprising contacting the cell(s) with a complex of FGF19 and FGFBP3 or a variant thereof. Additional methods of the present invention comprise assessing the levels of Erk1/2 phosphorylation, both before and after contacting the cell(s) with the complexes of the present invention and determining the increase or decrease of Erk1/2 phosphorylation in response to the complexes of the present invention.

Recently, it was shown that FGF19 alone was able to induce phosphorylation of the p90 ribosomal S6 kinase (p90RSK), which is a downstream target of phosphorylated ERK1/2. In turn, phosphorylated p90RSK is known to phosphorylate both ribosomal protein S6 (rpS6) and the eukaryotic translation initiation factor 4B (eIF4B). It was also recently shown that FGF19 alone was able to induce phosphorylation of both rpS6 and eIF4B. Thus one embodiment of the present invention comprises methods of stimulating phosphorylation of p90RSK, rpS6 and/or eIF4B in cells. These methods of phosphorylating p90RSK, rpS6 and/or eIF4B comprise contacting the cells with FGFBP3 or a variant thereof, alone or in complex with FGF19, in an amount sufficient to stimulate phosphorylation thereof.

One target of a phosphorylated p90RSK is glycogen synthase kinase 3α and 3β (GSK3 kinases), which, when phosphorylated, are responsible for inhibition of glycogen synthase (GS). The GSK3 kinases are also inhibited or inactivated when they themselves are phosphorylated. Specifically, phosphorylated p90RSK inhibits or inactivates the GSK3 kinases which block the inhibition of GS. Once the inhibition of GS is removed, GS is activated and, in turn, can trigger production of glycogen. Thus one embodiment of the present invention is directed to methods of increasing glycogen production in a subject in need thereof, with the methods comprising administering a FGFBP3 or a variant thereof, alone or in complex with FGF19, in a subject in need thereof in an amount sufficient to stimulate production of glycogen.

Phosphorylated p90RSK also stimulates protein synthesis at least in the liver. Accordingly, one embodiment of the present invention is directed towards increasing protein synthesis in a subject in need thereof, with the methods comprising administering FGFBP3 or a variant, alone or in complex with FGF19, thereof to the subject in an amount sufficient to stimulate protein synthesis. One example of a liver-synthesized protein is albumin. Accordingly, one specific embodiment of the present invention is directed towards increasing production of albumin in a subject in need thereof, with the methods comprising administering FGFBP3 or a variant thereof, alone or in complex with FGF19, to the subject in an amount sufficient to stimulate production of albumin.

Likewise, the present invention provides methods of stimulating promoter activity in a cell or population of cells, where the promoter is responsive to activated Erk1/2 or p90RSK with the methods comprising contacting the cell(s) with FGFBP3 or a variant thereof, alone or in complex with FGF19. One of skill in the art would be aware of promoters that respond to activated Erk1/2 or p90RSK. The activity of a variant of FGFBP3, alone or in complex with FGF19, with respect to stimulating Erk1/2-responsive promoters or p90RSK-responsive promoters may or may not be altered relative to the variant's ability to complex with FGF19. One of skill in the art can readily determine if a promoter is more or less activated over control groups using well known techniques such as transcription of reporter genes, ELISA assays, etc. Additional methods of the present invention comprise assessing the activity of an Erk1/2-responsive promoter both before and after contacting the cell(s) with the FGFBP3 or variant thereof, alone or in complex with FGF19, of the present invention and determining the increase or decrease of the promoter in response to the FGFBP3 or variant thereof, alone or in complex with FGF19, of the present invention.

The present invention also provides methods of altering the activity or expression of cell signaling molecules in a cell or population of cells in which there is a need to alter the expression or activity thereof. For example, contacting the cell or cells with FGFBP3 or a variant thereof, alone or in complex with FGF19, causes a reduction in the activity and/or expression of the CYP7A1 enzyme (Cholesterol 7α-hydrolase), a reduction in the activity or expression of glucose-6-phosphatase (G6PC), and/or a reduction in the activity or expression of peroxisome proliferator-activated receptor-γ coactivator-1β (PPARGC1B). In another example, contacting the cell or cells with FGFBP3 or a variant thereof, alone or in complex with FGF19, causes an increase in the activity and/or expression of interleukin-6 (IL-6), an increase in the activity and/or expression of insulin receptor substrate (IRS2) and/or an increase in the activity and/or expression of suppressor of cytokine signaling 3 (SOCS3). In other embodiments, the methods comprise contacting a cell or cells with FGFBP3 or a variant thereof, alone or in complex with FGF19, to a cell or cell in need thereof to alter the phosphorylation state of cell signaling molecules such as but not limited to AKT, STAT3 and forkhead box O1 (FoxO1). Specifically, contacting the cells with FGFBP3 or a variant thereof, alone or in complex with FGF19, will cause an increase in levels of phosphorylated AKT, STAT3 and/or FoxO1.

As used herein, "contacting," when used in connection with the methods of the present invention means bringing the compounds or compositions of the present invention in proximity to the target cells such that a specific binding event or a biological effect is possible. Thus, contacting can include adding the FGFBP3 in culture medium and applying the culture medium to cells in culture. Of course, contacting would also include administration of the FGFBP3, or pharmaceutical compositions thereof, of the present invention to cells in an intact organism. Compositions for administering the FGFBP3 of the present invention have been described herein.

As used herein, "administering," and "administer" are used to mean introducing FGFBP3 or variant thereof, alone or in complex with FGF19, of the present invention into a subject. When administration is for the purpose of treatment, the composition is provided at, or after the onset of, a symptom or condition in need of treatment. The therapeutic administration of this composition serves to attenuate any symptom, or prevent additional symptoms from arising. When administration is for the purposes of preventing a condition from arising ("prophylactic administration"), the composition is provided in advance of any visible or detectable symptom. The prophylactic administration of the composition serves to attenuate subsequently arising symptoms or prevent symptoms from arising altogether. The route of administration of the composition includes, but is not limited to, topical, transdermal, intranasal, vaginal, rectal, oral, subcutaneous intravenous, intraarterial, intramuscular, intraosseous, intraperitoneal, epidural and intrathecal as previously disclosed herein.

Furthermore, the methods would also include coadministering one or more substances in addition to the composition the present invention. The term "coadminister" indicates that each of at least two substances, with one of the substances being FGFBP3 or a variant thereof, alone or in complex with FGF19, is administered during a time frame wherein the respective periods of biological activity or effects of each of the substances overlap. Thus the term includes sequential as well as coextensive administration of the FGFBP3 of the present invention with another substance. And similar to administering the compositions of the present invention, coadministration of more than one substance can be for therapeutic and/or prophylactic purposes. If more than one substance is coadministered, the routes of administration of the two or more substances need not be the same.

The invention also relates to methods of lowering blood glucose levels in a subject, the method comprising administering FGFBP3 to a subject in need of lowering of blood glucose levels. In one embodiment, the subject is screened prior to administration of the FGFBP3.

The invention also relates to methods of lowering a subject's body weight, the method comprising administering FGFBP3 or a variant thereof to a subject that is in need of lowering its body weight. In one embodiment, the subject is screened prior to administration of the FGFBP3.

The invention also relates to methods of lowering blood glucose levels in a subject, the method comprising administering a complex of FGF19 and FGFBP3 to a subject in need of lowering of blood glucose levels. In one embodiment, the subject is screened prior to administration of the complex.

The invention also relates to methods of lowering a subject's body weight, the method comprising administering a complex of FGF19 and FGFBP3 to a subject that is in need of lowering its body weight. In one embodiment, the subject is screened prior to administration of the complex.

The following examples are illustrative and are not intended to limit the scope of the invention described herein.

EXAMPLES

Materials and Methods

Human BP3 cDNA, (the amino acid sequence of SEQ ID NO:2 and corresponding to amino acids 27-258 of SEQ ID NO:1), and the C-terminal hBP3 region (SEQ ID NO:4 and corresponding to amino acids 167-232 of SEQ ID NO:2), were subcloned into a pMAL-p2X vector (New England BioLabs, Ipswich, Mass.) and MBP-tagged recombinant proteins (hBP3 and C66, respectively) were generated as has been previously described in Xie, B., et al., *J. Biol. Chem.* 281, 1137-1144 (2006). MBP and MBP-BP3 are referred to herein as "control" and "BP3", respectively. Recombinant proteins were purified by fast protein liquid chromatography (FPLC). Briefly, bacterial cell lysates were loaded onto an MBPTrap™ HP columns (Dextrin Sepharose) (GE Healthcare Life Sciences, Piscataway, N.J.) and MBP-tagged proteins eluted with 20 ml of a gradient of 0-10 mM Maltose in Column Buffer (20 mM Tris HCl pH 7.4, 200 mM NaCl, 1 mM EDTA). Positive fractions were then loaded onto HiTrap™ Heparin HP columns (GE Healthcare Life Sciences) and proteins eluted with 20 ml of a gradient of 0-1.5M NaCl in Column Buffer. Eluted proteins were analyzed by immunoblotting with an anti hBP3 rabbit polyclonal antibody (Abgent, San Diego, Calif.) or with an anti MBP mouse monoclonal antibody (New England BioLabs). Eluted hBP3 was resolved on a 4-12% Bis-Tris gel (Life Technologies, Carlsbad, Calif.), visualized by Coomassie Blue staining and the bands excised from the gel. Mass spectrometry analysis was conducted as described previously in Zhang, W. et al., *J. Biol. Chem.*, 283:28329-28337 (2008).

MaxiSorp™ microtiter plates (Sigma Aldrich, St. Louis, Mo.) were coated with 100 µl/well of recombinant proteins [human recombinant FGF2 (Life Technologies), human recombinant FGF19, or human recombinant FGFR4 Fc Chimera (R&D Systems Minneapolis, Minn.); 7.5 µg/ml] and incubated overnight at 4° C. Plates were washed thrice between each incubation step with washing buffer [1× Phosphate buffered saline (PBS) with 0.2% Tween 20, pH 7.4 (PBST)]. Blocking was carried out with 100 µl/well of 5% dry milk diluted in PBST for 1 hour at room temperature. Subsequently, plates were incubated for 2 hours at room temperature with 100 µl/well of an MBP-tagged recombinant protein (MBP control or BP3) at a fixed concentration (1 µg/ml) or in serial dilutions. Detection was carried out with 100µ/well of an anti MBP mouse monoclonal antibody (New England BioLabs) and with an affinity-purified goat anti-mouse horseradish peroxidase (HRP)-conjugated antibody (GE Healthcare Life Sciences) (1:1,000 dilution in PBS). The reactions were visualized with the aid of 1-Step Turbo TMB (Thermo Scientific, Pittsburgh, Pa.), according to the manufacturer's protocol, and read with an Ultramark Microplate Imaging System (Bio-Rad Laboratories, Hercules, Calif.) at 450 nm absorbance.

MaxiSorp™ microtiter plates were coated with 0.75 mg of recombinant FGFR4 and incubated overnight at 4° C. Plates were washed thrice between each incubation step with PBS. Blocking was carried out with 100µ/well of 5% dry milk diluted in PBS for 1 hour at room temperature. Subsequently, plates were incubated for 2 hours at room temperature with 100µ/well of FGF19 (2µ/ml)±BP3 or MBP control (1µ/ml). Bound proteins were detected by western blot analysis with 1µ/ml of an anti FGFR4 (LD1; Genentech, South San Francisco, Calif.), anti MBP (New England BioLabs) or anti FGF19 (Abnova, Walnut, Calif.) mouse monoclonal antibodies.

Biacore T200 instrument (GE Healthcare) was used for surface plasmon resonance measurements. Human recombinant FGFR4 or FGFR1 Fc chimera in HBS-P buffer (0.01 M HEPES pH 7.4, 0.15 M NaCl, 0.05% P-20) were immobilized on a flow cell of a CM-5 sensor chip (GE Healthcare, Piscataway, N.J.) via amine coupling. A blank flow cell was used as a negative control for non-specific binding to the sensor surface. FGF19 (47.1 and 23.55 nM), C66 (245 nM) in HBS-P buffer, alone or in combination, or BP3 (4, 2, or 1 nM) were injected over the immobilized receptor with a flow rate of 10 4/min for 60 seconds and the resulting maximum responses were obtained. Dissociation constants were calculated from the association and dissociation rates of the proteins after washing. The experiments were performed in triplicate.

Six to nine week-old female ob/ob or C57BL mice were purchased from The Jackson Laboratory (Bar Harbor, Me.). Animals were maintained in a normal light-cycle room and were provided with rodent chow and water ad libitum. Mice were treated with a single intraperitoneal injection of recombinant proteins and blood glucose levels were determined with a portable glucose meter (Contour, Bayer, Whippany, N.J.) at different times after treatment (0-48 hours). Animal experiments were reviewed and approved by the Institutional Animal Care and Use Committee of Georgetown University.

Immunoprecipitation and Western Blot analyses were performed as described earlier in Tassi, E., et al., *Am. J. Pathol.*, 179:2220-2232 (2011). Briefly, livers from ob/ob or C57BL mice were homogenized in 1 mL of lysis buffer with a MagNa lyser homogenizer (Roche, Indianapolis, Ind.). 5 mg of total lysates were immunoprecipitated with 10 μl of sepharose-conjugated anti-AKT or phospho STAT3 antibodies and immunoblotted with an anti-phospho AKT or anti STAT3 rabbit polyclonal antibodies, respectively. Total AKT and STAT3 in the liver lysates (50 μg) were detected using an anti AKT and STAT3 rabbit polyclonal antibodies, respectively. ERK1/2 phosphorylation studies in HepG2 cells were performed by immunoblotting for phospho ERK1/2 and anti ERK1/2 rabbit polyclonal antibodies, as described in Tassi, E., et al., *J. Biol. Chem.*, 276:40247-40253 (2001). All antibodies were purchased from Cell Signaling (Danvers, Mass.). Detection of MBP and MBP-BP3 in mouse sera was carried out by immunoprecipitation and immunoblot with anti MBP magnetic beads and anti MBP rabbit polyclonal antibody (New England BioLabs), respectively.

Total RNA was isolated from ob/ob or C57BL mouse livers or WAT using RNeasy Mini kit or RNeasy Lipid Tissue kit (Qiagen, Valencia, Calif.), according to the manufacturer's instructions.

Liver total RNA was reverse transcribed into complementary RNA (cRNA), biotin-UTP labeled, and hybridized to the Illumina mouseRef-8v2.0 Expression BeadChip (Illumina Inc., San Diego, Calif.).

cDNA was synthesized from 1 μg of total RNA using the iScript™ cDNA Synthesis Kit, according to the manufacturer's protocol (Bio-Rad Laboratories, Hercules, Calif.). Real-time PCR was performed in a Realplex2 (Eppendorf, Hauppauge, N.Y.) using the iQ SYBR Green Supermix (Bio-Rad Laboratories) under the following conditions: 95° C. for 3 minutes, followed by 40 cycles (95° C. for 20 seconds, 60° C. for 30 seconds, and 72° C. for 40 seconds). The following PCR primers were used: mouse β-actin sense 5'-GGCGCTTTTGACTCAGGATTTAA-3' (SEQ ID NO: 7), antisense 5'-CCTCAGCCACATTTGTAGAACTTT-3' (SEQ ID NO: 8); mouse CYP7A1 sense 5'-CCCACAGT-TAATGCACTTGGATCCTG-3' (SEQ ID NO: 9) and antisense 5'-GGGCATGTAGAAATACTTCAGCTTGTTTCC-3' (SEQ ID NO: 10); mouse SOCS3 sense 5'-TCTTTGTCGGAAGACTGTCAACGG-3' (SEQ ID NO: 11) and antisense 5'-CATCATACTGATCCAGGAACTC-CCGA-3' (SEQ ID NO: 12); mouse IL6 sense 5'-GT-CACTTTGAGATCTACTCGGCAAACC-3' (SEQ ID NO: 13) and antisense 5'-TCTGACCACAGTGAGGAAT-GTCCA-3' (SEQ ID NO: 14); mouse G6PC 5'-CGACTCGCTATCTCCAAGTGA-3' (SEQ ID NO: 15) and antisense 5'-GTTGAACCAGTCTCCGACCA (SEQ ID NO: 16); mouse PPARGC1B 5'-TCCTGTAAAAGCCCG-GAGTAT-3' (SEQ ID NO: 17) and antisense 5'-GCTCTG-GTAGGGGCAGTGA-3' (SEQ ID NO: 18); mouse IRS2 5'-ACCGACTTGGTCAGCGAAG-3' (SEQ ID NO: 19) and antisense 5'-CACGAGCCCGTAGTTGTCAT-3' (SEQ ID NO: 20).

The web-based Ingenuity Pathways Analysis (IPA) (Ingenuity Systems®, www.ingenuity.com) was used to identify functional networks and pathways analyses. Activation z-score was calculated as a measure of functional and translational activation in Functions and Upstream regulators analysis. z-scores greater than 2 or smaller than −2 were considered significant.

Example 1

Six to nine week old female ob/ob mice, obtained from Jackson Laboratories, were randomly assigned to treatment groups with FGFBP3 alone, or FGF19 in combination with BP3. Ob/ob mice show pathologically increased glucose levels and exhibit glucose intolerance in traditional glucose tolerance tests. They are a leptin-deficient diabetes model.

The substances were administered by single intraperitoneal (i.p.) injection. To assess potential therapeutic effects on the metabolic profile with FGFBP3 or FGF19+FGFBP3 treatments, glucose levels were measured while the animals were fed ad libitum. Two series of experiments were performed to investigate acute and sustained effects with the different treatments.

Before starting the experiments, the animals were weighed to determine the amount of proteins (FGFBP3 or others) to inject. Contrary to alternative approaches that use glucose challenge after prolonged fasting (=glucose tolerance test), the animals were not fasted and were fed ad libitum. This was done to mimic the natural setting. For the measurements of blood glucose levels, blood was sampled from the tail tip at 0, 2, 3, 4 and 24 hours after protein injection. Blood glucose levels were determined with a portable glucose meter (Contour®, Bayer HealthCare).

The results in FIG. 1 show that the effects of FGFBP3 alone or FGF19+FGFBP3 treatments on glucose metabolism in ob/ob mice. Left Panel, shows that upon intraperitoneal injection of either FGFBP3 alone or FGF19+FGFBP3, glucose levels fell to roughly normal levels (100 to 150 mg/dl) within 2 hours after the first treatment. Levels stayed close to normal range (compared to controls) for 24 hours following injection. Right Panel, shows that FGFBP3 had a greater effect on lowering glucose levels when normalized to account for different baseline glucose levels.

Figure 2:
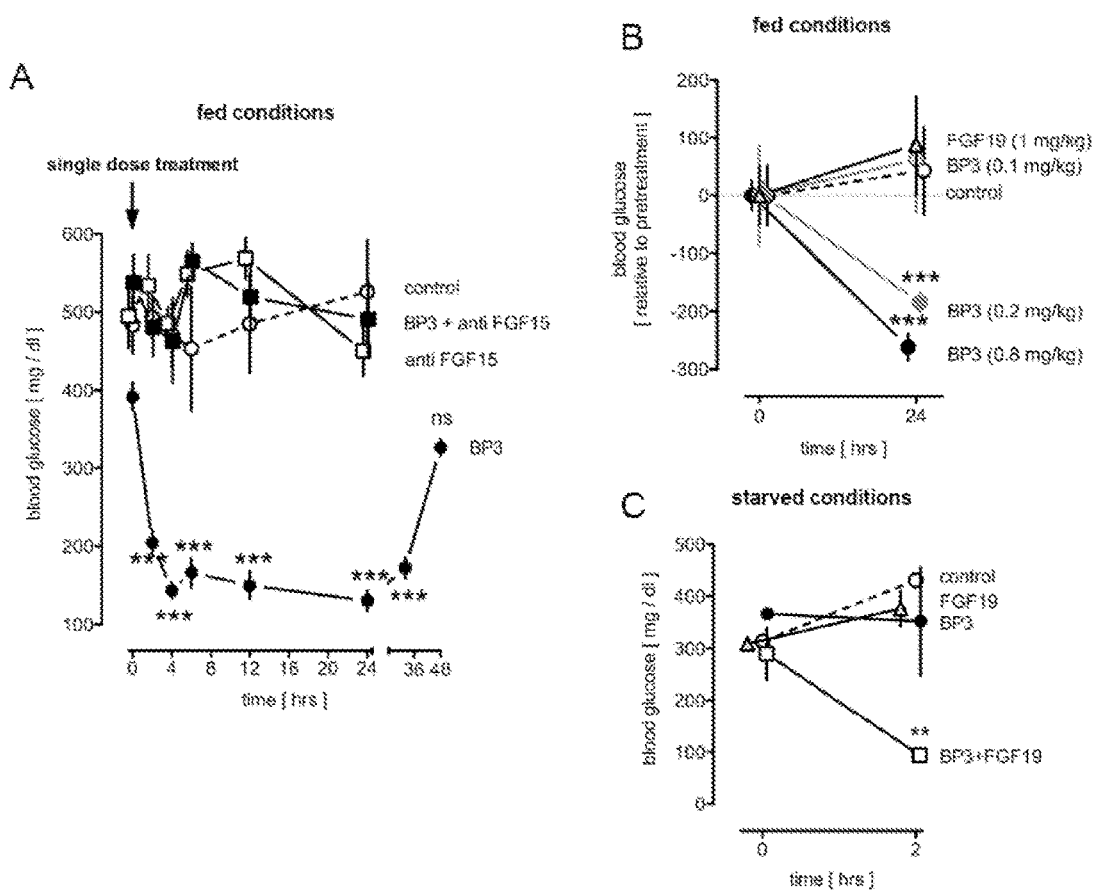
FIG. 2 depicts the effects of BP3 on glycemia in fed ob/ob mice. Blood glucose levels after treatment with a single intraperitoneal injection of BP3 or control protein (=MBP) ±pretreatment with an anti FGF15 antibody. Mean±SEM; n≥5 mice/group. ns, non significant; *, P<0.0001 vs. control (=MBP). B. Blood glucose levels in fed ob/ob mice 24 hours after a single intraperitoneal administration of increasing doses of BP3, FGF19 or control (=MBP). The values are calculated relative to baseline levels of blood glucose (mg/dl). Mean±SEM; n≥5 mice/group. *, P<0.0001 vs. control (=MBP). C. Blood glucose of short-term starved ob/ob mice 2 hours after treatment with a single intraperitoneal injection of BP3 (0.8 mg/kg), FGF19 (1 mg/kg), BP3+FGF19, and control (=MBP; 1 mg/kg). Mean±SEM; n=4 mice/group. **, P<0.001.

Treatment of the mice with an anti-FGF15 antibody and BP3 did not result in measurably different glucose levels compared to mice treated with the control protein only. Moreover, the effect of the antibody pretreatment did not significantly alter hyperglycemic levels when co-injected with a control protein at all time points (FIG. 2A).

A dose-response curve for BP3 was established and compared that to exogenous FGF19. The administration of a single high dose of FGF19 (1 mg/kg) did not impact hyperglycemia in the ob/ob mice, whereas BP3 treatment resulted in a dose-dependent decrease of blood glucose with an ED50 below 0.2 mg/kg (FIG. 2B). To evaluate if the BP3 effect was impacted by the feeding status of the animals, the effect of BP3 in starved animals, which have reduced FGF15 levels, was tested. In this setting, BP3 effects on glucose were absent and comparable to those of a single treatment of FGF19 or of the control protein. Normoglycemic levels were achieved when starved animals were co-treated with a combination of BP3 and exogenous FGF19 (FIG. 2C).

Figure 3:
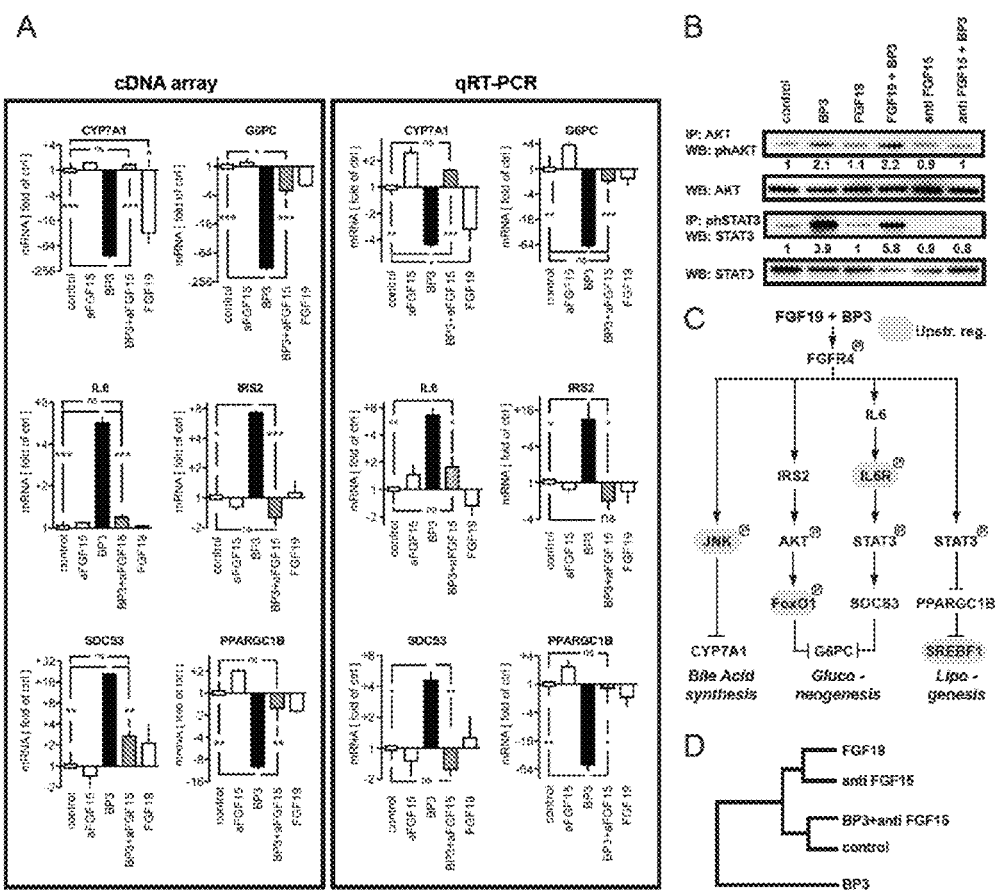
FIG. 3 depicts the ability of BP3 to inhibit gluconeogenesis through IRS2/AKT and IL6/STAT3-dependent downregulation of G6PC by modulating endogenous FGF15 activity. A. Changes in hepatic gene expression determined by cDNA array (left) versus qRT-PCR (right). Values are calculated as fold of control treatment levels. Mean±SEM, n=3/group. ns, non significant; *, P<0.05; , P<0.001; *, P<0.0001. B. AKT and STAT3 phosphorylation in ob/ob liver lysates from each experimental group were assayed by immunoprecipitation and western blot with phosphospecific antibodies. The expression of AKT and STAT3 were also determined by immunoblotting with specific antibodies. The numbers below the blots indicate the fold-change, corrected for the total protein expression. The blots are representative of three independent experiments. C. Schematic summary of the FGFR4-FGF19-BP3 regulatory pathways in liver tissue. Sensitization of FGFR4/FGF19 pathway by BP3 results in a downstream activation of IRS2/AKT and IL6/STAT3 signaling pathways, leading to the inhibition of gluconeogenesis, through G6PC downregulation. Likewise, activation of STAT3 results in an inhibition of PPARGC1B and SREBF1, leading to the inhibition of lipogenesis. Activation of FGFR4/FGF19 by BP3 also results in a suppression of bile acid biosynthesis through the downregulation of CYP7A1 gene. D. Hierarchical cluster analysis of gene expression in livers of fed ob/ob mice treated with recombinant human BP3, FGF19, anti FGF15, anti FGF15+BP3 or MBP control for 4 hours. The cluster analysis shows a separation of BP3 treatment from all other conditions (n=3 independent samples per group).

Gene expression patterns in livers of ob/ob mice using the treatment cohort above were assayed. Organs were harvested after four hours when the glucose lowering effect of BP3 had reached normoglycemic levels and included the following treatment groups: control protein (MBP), FGF19, BP3 alone, anti-FGF15 antibody alone, or BP3 plus anti-FGF15. As a signature gene of the FGFR4/FGF19 signaling axis CYP7A1 (Cholesterol 7α-hydrolase) was first probed for expression. CYP7A1 mRNA was reduced 32-fold after administration of exogenous FGF19 suggesting that control of CYP7A1 transcription in the liver in response to the postprandial secretion by ileal entherocytes of FGF15/19 activates FGFR4 in the hepatocytes, thereby resulting in the repression of bile acid (BA) biosynthesis is intact. Administration of exogenous FGF19 significantly reduced CYP7A1 transcription by 32 fold versus control mice, thus indicating the efficacy of FGF19 treatment. BP3 treatment, however, resulted in a more potent downregulation of CYP7A1, whose transcription was found reduced by 110 fold when compared to the expression levels observed in control mice. Moreover, the reduction of endogenous FGF15 levels by a specific neutralizing antibody blunted BP3-induced CYP7A1 inhibition, thereby indicating that BP3 can modulate FGF15/19-dependent gene regulation (FIG. 3A).

Interestingly, one of the most prominently downregulated genes in livers from BP3 treated mice was glucose-6-phosphatase (G6PC), a key gluconeogenic enzyme, which was reduced about 130 fold when compared to control levels. In addition, there were corresponding increases of G6PC upstream regulatory genes, such as insulin receptor substrate 2 (IRS2). BP3 treatment also resulted in a marked upregulation of both interleukin 6 (IL6) and its downstream effector, suppressor of cytokine signaling 3 (SOCS3), which in turn blocks gluconeogenesis through G6PC suppression. Lastly, it is known that FGF19/15 can negatively modulate lipogenesis in mouse livers by inhibiting peroxisome proliferator-activated receptor-γ coactivator-1β (PPARGC1B) expression. Here, BP3 treatment significantly enhanced this effect (FIG. 3A). In these experimental settings, whilst a single administration of FGF19 was not sufficient to alter the expression of these gluconeogenic or lipogenic genes, neutralization of endogenous FGF15 reverted BP3-induced gene regulation to levels indistinguishable from those observed in control livers. These microarray data were validated with qRT-PCR, and it was observed that the results were highly consistent with those obtained in the cDNA array, as shown in the right panel of FIG. 3A.

BP3's ability to modulate FGF15/19-induced downstream activity was examined. Specifically, the phosphorylation state of candidate signaling molecules upstream of gluconeogenesis and lipogenesis in the same ob/ob mouse livers was analyzed. Protein kinase B (AKT) is a critical effector kinase downstream of IRS2 whose phosphorylation results in a negative regulation of gluconeogenic genes, such as G6PC. Administration of BP3, but not of FGF19, induced a two-fold increase of AKT phosphorylation over the basal status in control levels, without affecting AKT expression. In addition, activation of AKT by BP3 was reduced to baseline intensities by an anti FGF15 antibody (FIG. 3B). The addition of exogenous FGF19 to BP3 treatment evoked a comparable AKT phosphorylation to that induced by BP3 only.

Several reports have described the contribution of interleukin-6 (IL6) pathway activation in improving insulin sensitivity through the activation of STAT3, with resulting G6PC downregulation. The status of endogenous STAT3 phosphorylation was examined in the same ob/ob mouse livers. Treatment with BP3, but not with FGF19, resulted in a 3.9-fold increase of STAT3 phosphorylation over baseline levels, whereas total STAT3 expression remained unchanged. Moreover, neutralization of endogenous FGF15 by a specific antibody blunted BP3-induced STAT3 phosphorylation (FIG. 3B). The graphic model depicted in FIG. 3C summarizes the molecular pathways utilized by BP3 to modulate BA biosynthesis, gluconeogenesis and lipogenesis in mouse livers.

To further compare the expression pattern of the hepatic genes between different treatments, a sample dendrogram was generated by hierarchical cluster analysis. The analysis revealed a clear separation between the BP3 treated liver samples and control groups, indicating that global gene expression in the former experimental group was significantly altered (FIG. 3D). It is noteworthy that the transcript pattern from livers co-treated with BP3 and a neutralizing anti FGF15 antibody clustered together with those of the control group, and they also co-clustered with transcripts from FGF19 or anti FGF15 treated mouse livers.

Figure 4:
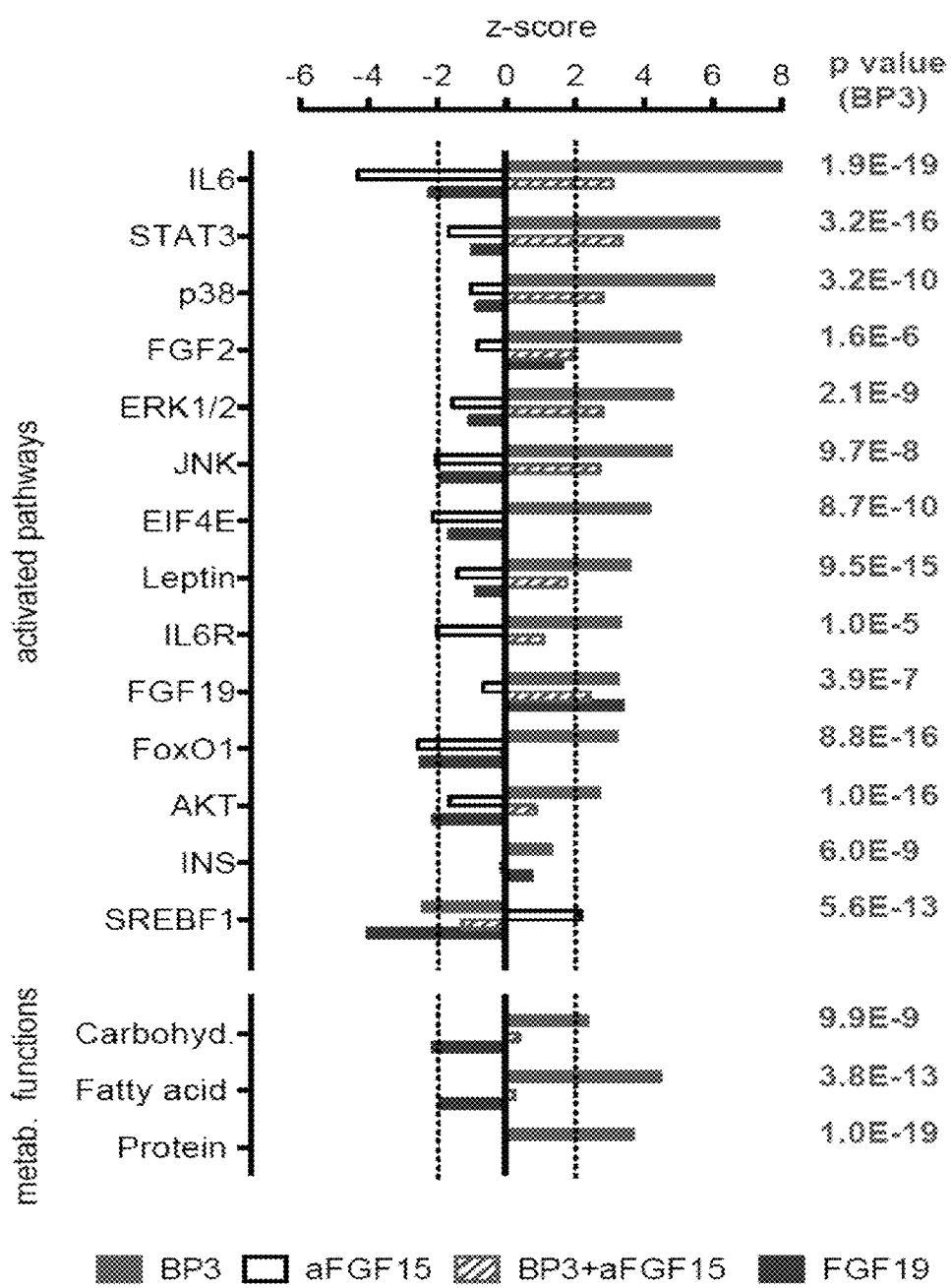
FIG. 4 depicts the driver pathways of BP3 effects. Ingenuity pathway analysis of the differentially expressed liver genes in ob/ob mice treated with BP3, anti FGF15, BP3+anti FGF15 (striped bar) or FGF19 and normalized to the control group (=MBP). Upper panel: Z-score predicting the activation of signaling pathways based on Ingenuity upstream regulator analysis. Lower panel: Z-score predicting the activation of metabolic functions identified by Ingenuity global function analysis. Z-scores smaller (inhibited) or greater (activated) than 2 were considered biologically significant and are represented by dashed lines. The respective P-values for the Z-scores are stated on the right.

The Ingenuity Pathway Analysis software was used to integrate gene expression with key biochemical networks in response to the different experimental treatments (FIG. 4). An overall analysis of metabolic functions indicated that carbohydrate, fatty acid and protein metabolism were significantly activated in response of BP3 treatment, but not of FGF19 alone (FIG. 4, bottom). Analysis of activated pathways revealed a significant activation of FGF2 and FGF19-induced signaling after BP3 treatment. Moreover, major biochemical effector molecules activated by the engagement of FGF/FGFR axes, such as p38, ERK1/2 and JNK, were significantly activated. Amongst all others, the IL6/STAT3 signaling pathway showed the highest induction upon BP3 administration, with z-scores of 7.98 and 6.15, respectively. Commensurate with an upregulation of IL6, IL6 receptor (IL6R)-induced downstream signaling was also enhanced.

Activated AKT phosphorylates the downstream forkhead box O1 (FoxO1) transcription factor, which results in the suppression of gluconeogenic gene transcription, such as G6PC. Both AKT and FoxO1 pathways are concomitantly activated with BP3 treatment, whereas treatment with FGF19 alone or an anti-FGF15 antibody maintains these pathways in an inhibitory state. Commensurate with BP3-mediated suppression of PPARGC1B transcription via STAT3 activation (FIG. 3A), BP3 treatment induced the inhibition of sterol regulatory element-binding protein 1c (SREBF1) signaling pathway, a PPARGC1B downstream effector molecule, thus indicating a reduction of lipogenesis.

It has been reported that FGF19 can promote initiation of protein translation in mouse livers by inducing eukaryotic initiation factor 4E (EIF4E) phosphorylation. Here, the EIF4E pathway was highly activated in response to BP3 administration, whereas FGF19 alone failed to activate it.

It is also noteworthy that BP3 treatment in leptin deficient ob/ob mice significantly restored leptin-induced signaling pathway, thus suggesting that BP3 can trigger a downstream molecular response that mimicks that of leptin. Neutralization of endogenous FGF15 drastically reduced the induction of the aforementioned pathways and metabolic functions upon BP3 treatment, thus indicating that BP3 can sensitize and modulate FGF15/19-driven downstream biochemical signaling. The integration of BP3/FGF19/FGFR4-induced transcriptional regulation with activated pathways analyzed in silico is depicted in the schematic model in FIG. 3C.

Example 2

Figure 5:
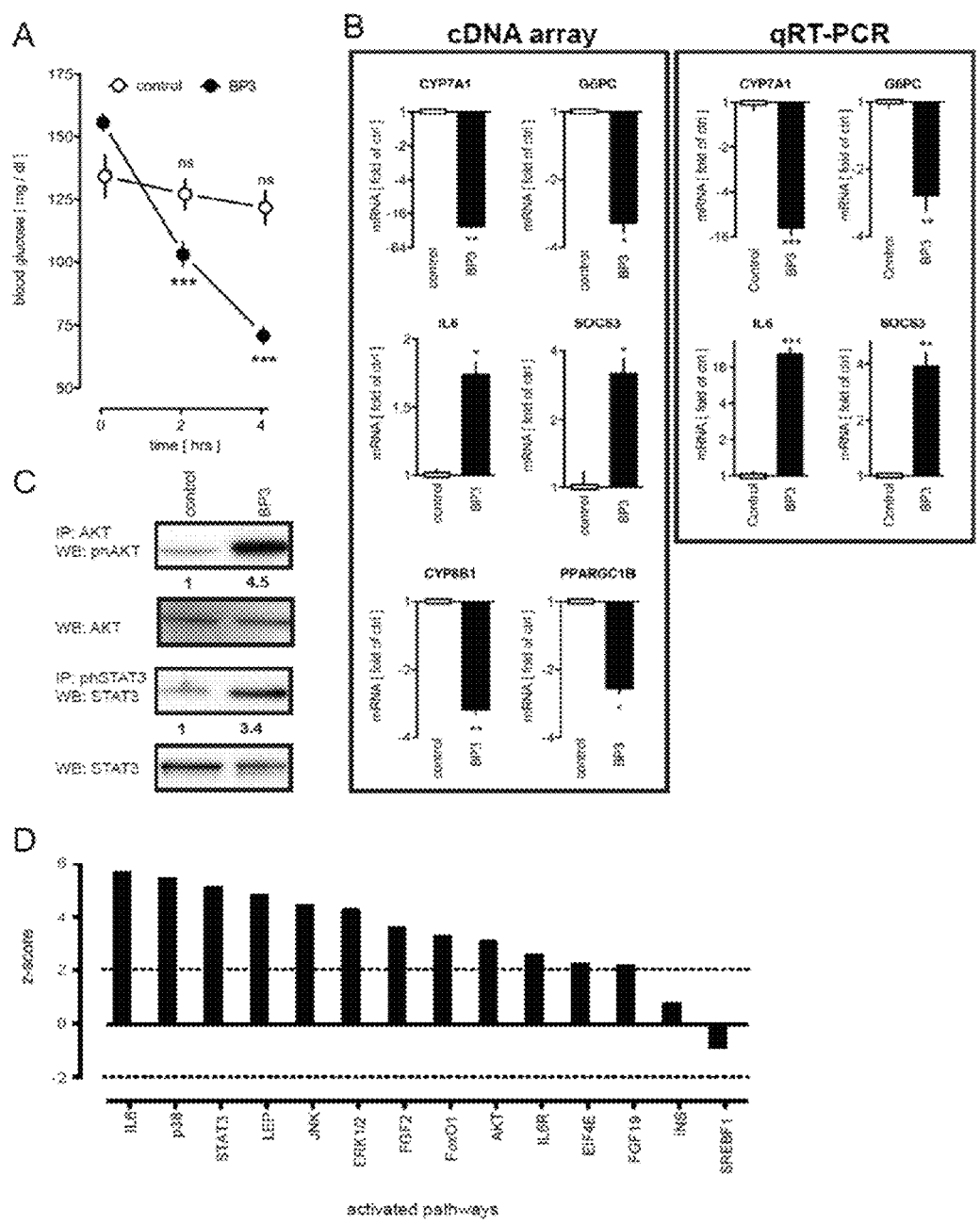
FIG. 5 depicts the ability of BP3 to reduce blood glucose levels in fed, healthy, non-diabetic C57BL mice. A. Blood glucose levels of fed C57BL mice treated with a single intraperitoneal injection of BP3 or MBP control (0.8 mg/kg). Blood glucose was measured at 2 and 4 hours after administration. Mean±SEM; n=3. *, P<0.05; , P<0.001; *, P<0.0001. B. Changes in hepatic gene expression determined by qRT-PCR (right) versus cDNA array (Illumina) (left). Values are calculated as fold of MBP control levels. Mean±SEM, n=2. *, P<0.05; , P<0.001; *, P<0.0001. C. C57BL mice were administered MBP or BP3 (0.8 mg/kg) by intraperitoneal injection for four hours. AKT and STAT3 phosphorylation in liver lysates were assayed by immunoprecipitation and western blot with specific antibodies. The expression of total AKT and STAT3 were also determined by immunoblotting with specific antibodies. The numbers below the blots indicate the fold-change, corrected for the total protein expression, relative to the control group. The blots are representative of three independent experiments. D. Ingenuity pathway analysis of the differentially expressed genes in C57BL mouse livers treated with BP3 and normalized to the MBP control group. Z-score predicting the activation of signaling pathways based on Ingenuity upstream regulator analysis. Z-scores smaller (inhibited) or greater (activated) than 2 were considered biologically significant and are represented by dashed lines.

The impact of BP3 treatment on ad libitum fed normoglycemic wild type C57BL mice was examined using a similar protocol as above. Similar to the results seen in the ob/ob mice, a single intraperitoneal dose of BP3, but not of a control protein, was sufficient to significantly reduce plasma glucose levels (FIG. 5A). Similar to what observed in ob/ob mouse livers, BP3 treatment of wild type mice induced a marked downregulation of hepatic CYP7A1, CYP8B1, G6PC, and PPARGC1B, and an upregulation of IL6 and SOCS3 (FIG. 5B) and a prominent increase of endogenous AKT and STAT3 phosphorylation levels, without affecting basal expression (FIG. 5B). Conversely, CYP8B1 transcription was not suppressed by BP3 treatment in ob/ob mice. Lastly, in this experimental setting, in silico analysis of BP3-activated pathways in C57BL mice (FIG. 5D) was commensurate with the results obtained from the ob/ob model (see FIG. 4).

Example 3

Figure 6:
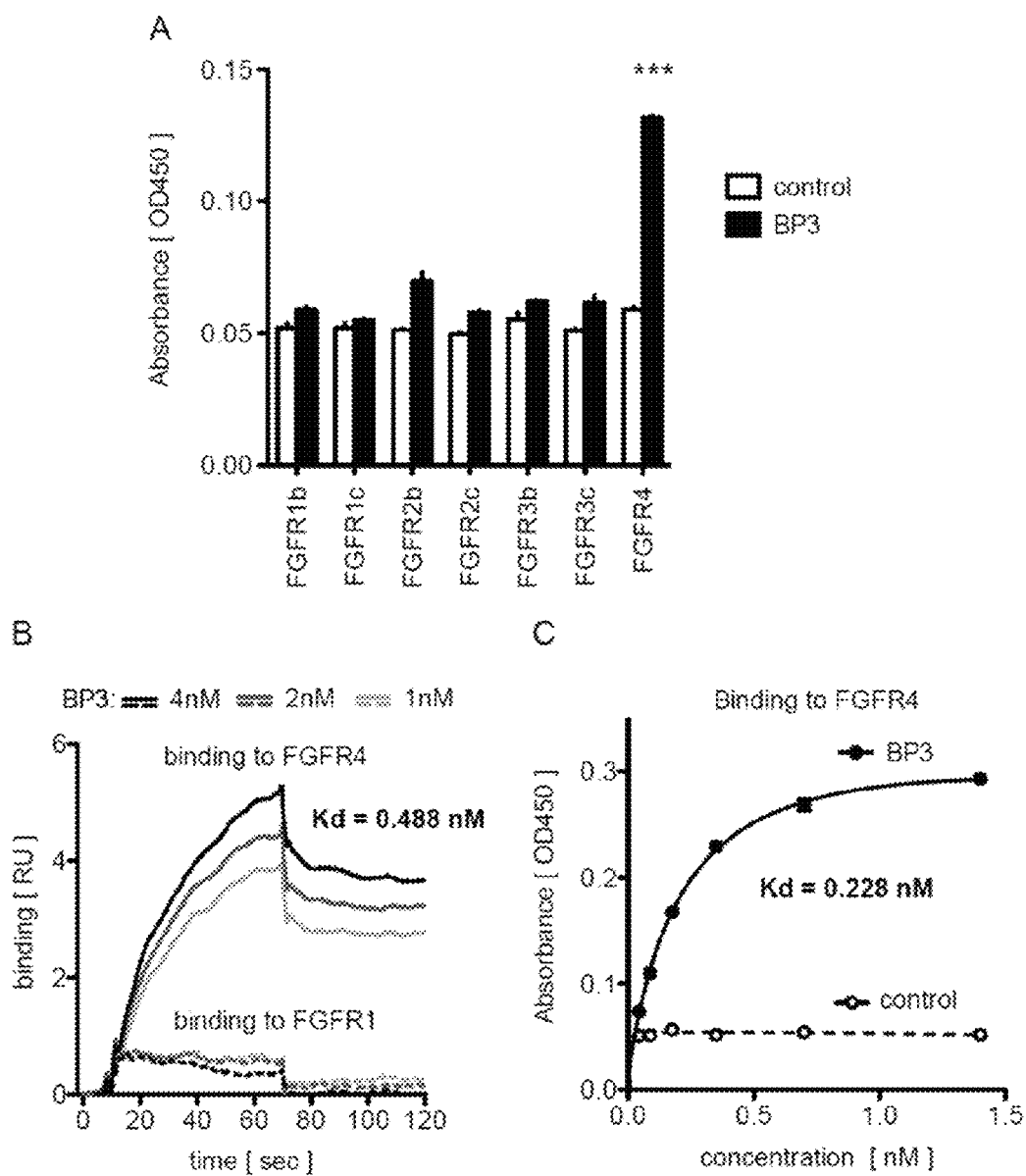
FIG. 6 depicts the ability of BP3 to selectively bind to FGFR4. A. Binding of BP3 or MBP (ctrl) to immobilized FGFRs was measured by direct ELISA with an anti MBP antibody. Mean±SEM of one of three independent experiments done in duplicate. *, P<0.0001 BP3 (black bars) vs. MBP ctrl (white bars). B: SPR sensorgrams illustrating the binding kinetics of BP3 to immobilized FGFR4 and FGFR1. The concentration of the BP3 analyte was varied from 4 to 1 nM. RU, response units. C: Binding of increasing concentrations of BP3 or MBP to immobilized FGFR4 measured by direct ELISA with an anti MBP antibody. Mean±SEM of one of three independent experiments done in duplicate
Figure 7:
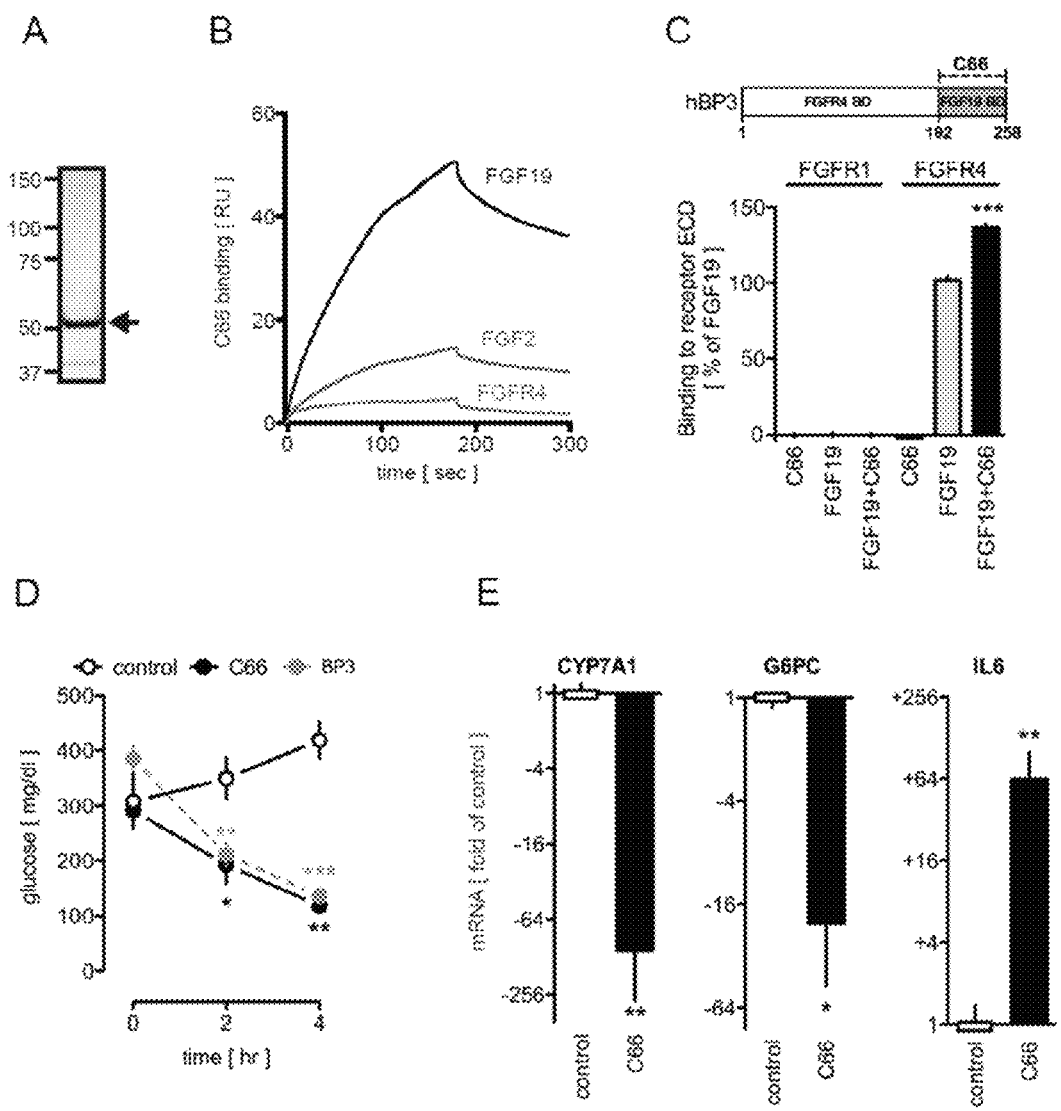
FIG. 7 depicts that the C-terminal 66-amino acid long FGF-binding domain of BP3 ("C66") is sufficient to reduce hyperglycemia in diabetic mice and to stabilize FGFR4/FGF19 complex formation. A. Coomassie blue staining of MBP-tagged C66 fusion protein purified by amylose affinity chromatography. The arrow indicates a band of an apparent molecular mass of 52 kDa. B. SPR sensorgrams illustrating the binding of C66 to immobilized FGF19, FGF2 and FGFR4. RU, response units. C. Schematic representation of human BP3. The numbers correspond to the human BP3 amino acid sequence (upper panel). Equilibrium binding of FGF19, C66 or their combination to immobilized FGFR1 or FGFR4 was analyzed by SPR (lower panel). Mean±SEM of three independent experiments. Data are represented as percent difference to FGF19 binding to FGFR1 or FGFR4. *, P<0.0001, FGF19+C66 vs. FGF19. D. Effect of C66 on glycemia in ob/ob mice. Blood glucose levels of fed ob/ob mice treated with a single intraperitoneal injection of C66, BP3 or MBP control (0.8 mg/kg). Blood glucose was measured at 2 and 4 hours after administration. Mean±SEM; n=3-11 mice/group. *, P<0.05; , P<0.001; *, P<0.0001. top asterisks: BP3 vs. MBP; bottom asterisks: C66 vs. MBP. E. Changes in hepatic gene expression determined by qRT-PCR in fed ob/ob mice treated with MBP and C66 for 4 hours. Values are calculated as fold of MBP control levels. Mean±SEM, n=3/group. *, P<0.05; **, P<0.001.

FGF19 exhibits a high affinity for FGFR4, and BP3 can enhance FGFR4/FGF19 complex formation. The data herein shows that BP3 binds to FGFR4, but not to other FGFR5 (FIG. 6A), and contains a high-affinity binding site for FGFR4, as determined in a dose response assay by surface plasmon resonance (SPR) and ELISA (FIG. 6B-C). A 66 amino acid-long BP3 C-terminal fragment has been previously identified as the FGF2 binding domain. This binding domain was purified, and an MBP-tagged C66 fusion protein (referred as C66) (FIG. 7A) and used as a tool for binding studies. Whilst C66 retained its ability to bind to FGF2, its binding to FGF19 was even higher. The C66 fragment, however, did not bind to FGFR4, indicating that the FGF-binding domain of BP3 is not sufficient to elicit BP3 binding to FGFR4 (FIG. 7B). The contribution of C66 to FGFR4/FGF19 complex formation was assessed in vitro. C66 significantly enhanced FGF19 binding to immobilized FGFR4, but immobilized FGFR1 did not display any binding to FGF19 or C66, either alone or in combination, which is similar to the binding characteristics of full length BP3 (FIG. 7C). Moreover, when administered to ad libitum fed ob/ob diabetic mice for four hours in a single dose, C66 reverted hyperglycemia to normoglycemic levels, indistinguishable from those resulted from the treatment with full-length BP3, whereas mice treated with a control protein remained diabetic (FIG. 7D). Analogous to full-length BP3 treatment, gene expression analysis of livers from C66-treated ob/ob mice revealed a marked suppression of CYP7A1 and G6PC and upregulation of IL6 (FIG. 7E). From these experiments, the FGF-binding domain of BP3 is sufficient to increase FGFR4/FGF19 binding affinity and to reduce hyperglycemia in diabetic mice to the same extent as full-length BP3. Moreover, binding of BP3 to FGFR4 is not required for BP3 regulation of glucose homeostasis.

Example 4

Five week old female ob/ob mice, obtained from Jackson Laboratories, were randomly assigned to treatment groups with FGF19 alone, or FGF19 in combination with BP3. The substances were administered in the morning by single intraperitoneal (i.p.) injection. To assess potential therapeutic effects on the metabolic profile with FGF19 or FGF19+BP3 treatments, glucose tolerance tests were performed and changes in body weights were measured. Two series of experiments were performed to investigate acute and sustained effects with the different treatments.

| Series I | Series II |
|---|---|
| 1. Baseline (non-treated) | 1. Baseline |
| 2. FGF19 or FGF19 + BP3 treated | 2. Post-treatment (2 days |

| Series I | Series II |
|---|---|
| (1 dose/day for 5 days) | following a single dose) |
| 3. Post-treatment (9 days after treatment) | |

Figure 8:
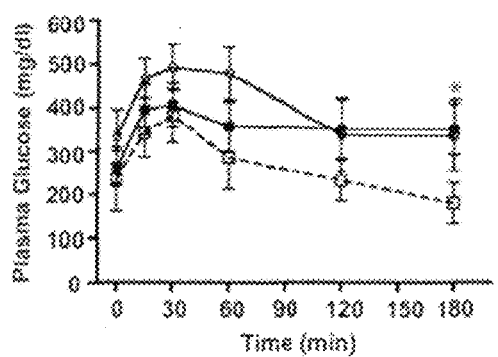
FIG. 8 depicts the effects of multiple FGF19 or FGF19+BP3 treatments on glucose blood levels in ob/ob mice after a bolus injection of glucose (=glucose tolerance test). A, Five treatments with FGF19 reduced blood glucose levels at 180 minutes after the beginning of the glucose tolerance test, and the curve returned to the baseline 9 days after receiving no treatment. Filled Squares: Baseline; Open Squares: FGF19 (one dose per day for 5 days); Open Circles: FGF19 (one dose per day for 5 days+9 days of no treatment). B, Five treatments with FGF19+BP3 improved the glucose tolerance at 60, 120, and 180 minutes with a sustained effect for 9 days. Filled Squares: Baseline; Open Squares: FGF19+BP3 (one dose per day for 5 days); Open Circles: FGF 19+BP3 (one dose per day for 5 days+9 days of no treatment). C, The area under the curve of the glucose tolerance test (AUC) was improved after 5 treatments in both groups. After another 9 days without any treatment, only the FGF19+BP3 group exhibited an improved glucose tolerance test. Solid Bars: Baseline, Open Bars: FGF19 or FGF19+BP3 (one dose per day for 5 days); Hatched Bars, FGF19 or FGF19+BP3 (one dose per day for 5 days+9 days of no treatment). * denotes P<0.01.
Figure 8:
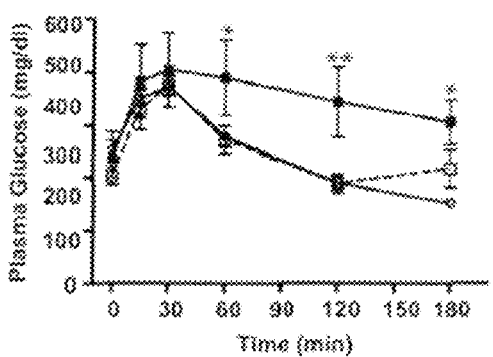
Figure 8:
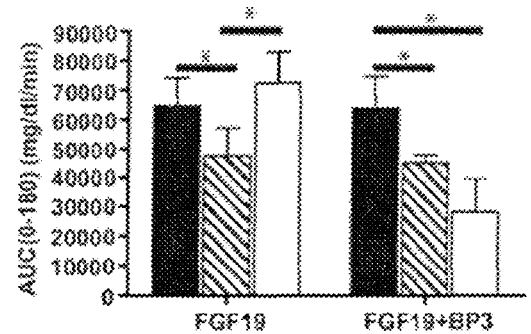
Figure 9:
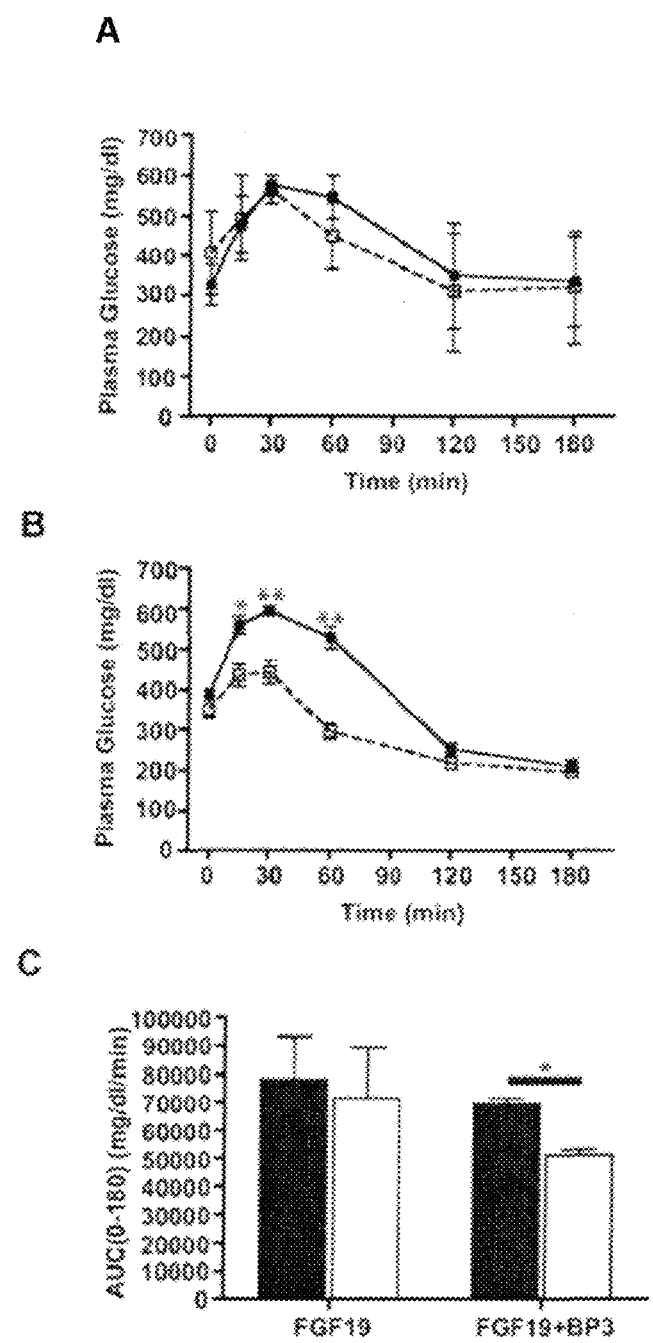
FIG. 9 depicts the effects of a single dose of FGF19 or FGF19+BP3 treatment on glucose blood levels in ob/ob mice after a bolus injection of glucose (=glucose tolerance test). A, The glucose levels were not changed 2 days after a single dose of FGF19 alone. Filled Squares: Baseline, Open Squares: single dose treatment. B, In the FGF19+BP3 group, the glucose levels were significantly reduced at 15, 30 and 60 minutes post-injection of glucose. C, The area under the curve of the glucose tolerance test (AUC) was reduced 2 days after a single treatment in FGF19+BP3 group. Filled Squares: Baseline, Open Squares: Single treatment. * denotes P<0.05, ** P<0.01.
Figure 10:
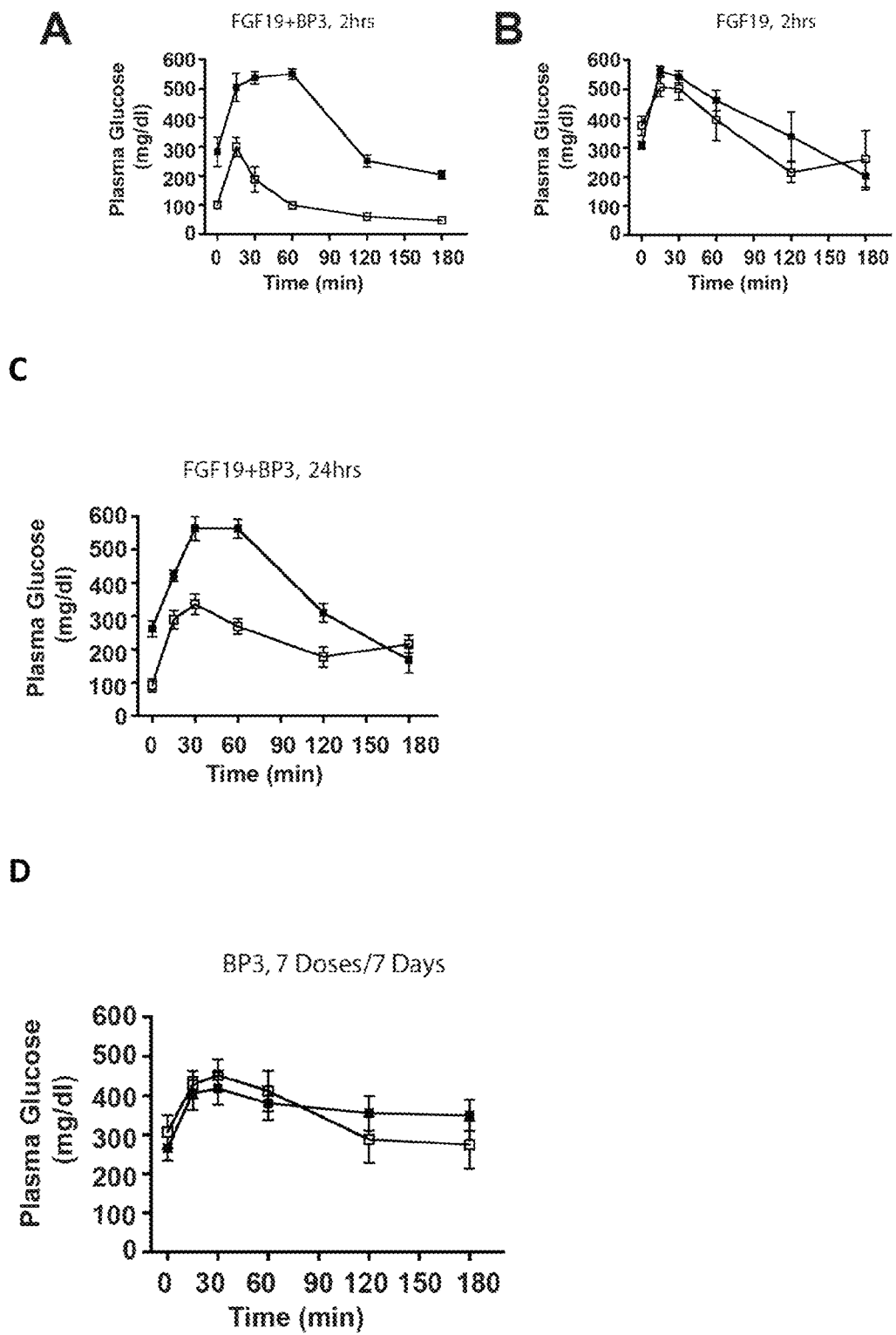
FIG. 10 depicts the effects of acute single doses of BP3, FGF19, and the complex of BP3+FGF19 in ob/ob mice in response to a glucose tolerance test.

For all experiments reported in FIGS. 8-10, mice were fasted overnight (14 h) before they were subjected to a standard glucose tolerance test (GTT). The GTT is used to evaluate the ability of an organism to metabolize exogenous glucose. In clinical practice the GTT is used to uncover patients with latent diabetes or patients at risk for diabetes, e.g. during pregnancy and is performed after a fasting period by oral administration of a glucose containing drink. In the animal model oral GTT is performed by gavage of a glucose solution, i.e. orally administration. Intraperitoneal injection of a sterile glucose solution was chosen because this allows for a tighter control of dosing of the glucose. Before starting the experiments, the animals were weighed to determine the amount of glucose to inject. The glucose tolerance test was performed in a quiet room and handling was kept down to a minimum to reduce stress during the procedure. A bolus of glucose (1 g/kg) was injected into the intraperitoneal cavity (30% D-glucose:$H_2O$ solution) and blood was sampled from the tail tip at 0, 15, 30, 60, 120 and 180 minutes after glucose injection. Blood glucose levels were determined with a portable glucose meter (Contour®, Bayer HealthCare).

Ob/ob mice exhibit glucose intolerance and are generally used as a leptin-deficient diabetes model and reflect the human disease well. To examine the metabolic capacity of the animals for glucose the intraperitoneal glucose tolerance test (IPGTT) was performed in ob/ob mice and blood glucose levels were read at 0, 15, 30, 60, 120 and 180 minutes post-injection of glucose. The baseline blood glucose levels were much higher than the normal range (70-120 mg/dl) (FIG. 8A, 8B, Baseline). After 5 days of treatment (one dose/day) with FGF19, ob/ob mice (n=6) showed an improved glucose tolerance as evidenced by reduced blood glucose levels at 180 minutes post-injection of glucose ($p<0.05$). The glucose tolerance test (IPGTT) was repeated 9 days after treatment and glucose levels returned to the levels seen before the treatment (FIG. 8A).

For the combination treatment group (FGF19+BP3, n=5), the glucose tolerance test (IPGTT) was seen improved at 60, 120 and 180 minutes post-injection of glucose ($p<0.05$). The respective blood glucose levels were significantly lower than those of the control group. This effect was sustained even 9 days after the last of 5 doses of FGF19+BP3 (FIG. 8B). The results from the glucose tolerance test, shown as the area under the curve of the blood glucose levels after glucose injection (AUC), was reduced by 26% compared with baseline in the FGF19 group and by 33% in the FGF19+BP3 group. Most strikingly, the FGF19+BP3 group displayed an improved AUC compared with baseline even 9 days after completed treatment ($p<0.01$), whereas no such effect was observed in mice receiving FGF19 alone (FIG. 8C). In addition, the combination treatment (n=5) improved the AUC even 2 days after a single dose of FGF19+BP3, while FGF19 alone (n=3) did not ($p<0.01$, FIG. 9). These data suggest that BP3 dramatically enhances the FGF19 effect in a standardized IPGTT glucose tolerance test in diabetic mice.

The effects of acute single doses of BP3 or FGF19 alone, and the combination of BP3+FGF19 were tested in ob/ob mice by IPGTT described above (FIG. 10A, B). Mice were starved overnight (14 hours) and then treated for two hours by i.p. injection of vehicle (filled squares, FIG. 10A,B) or FGF19 alone or BP3+FGF19 (open squares FIG. 10A,B). The IPGTT test was initiated two hours after treatments. The combination of BP3+FGF19 induced a striking effect and normalized the baseline blood glucose and the IPGTT blood glucose curve (FIG. 10A). This effect was still present 24 hours after the single dose of BP3+FGF19 (FIG. 10C). FGF19 alone showed no significant effect in the test (FIG. 10B). Also, treatment of animals with BP3 alone (without FGF19) showed no significant effect, and even 7 days of dosing of BP3 with a single daily dose of BP3 lacked an effect on the baseline blood glucose or on the IPGTT test (FIG. 10D).

Figure 11:
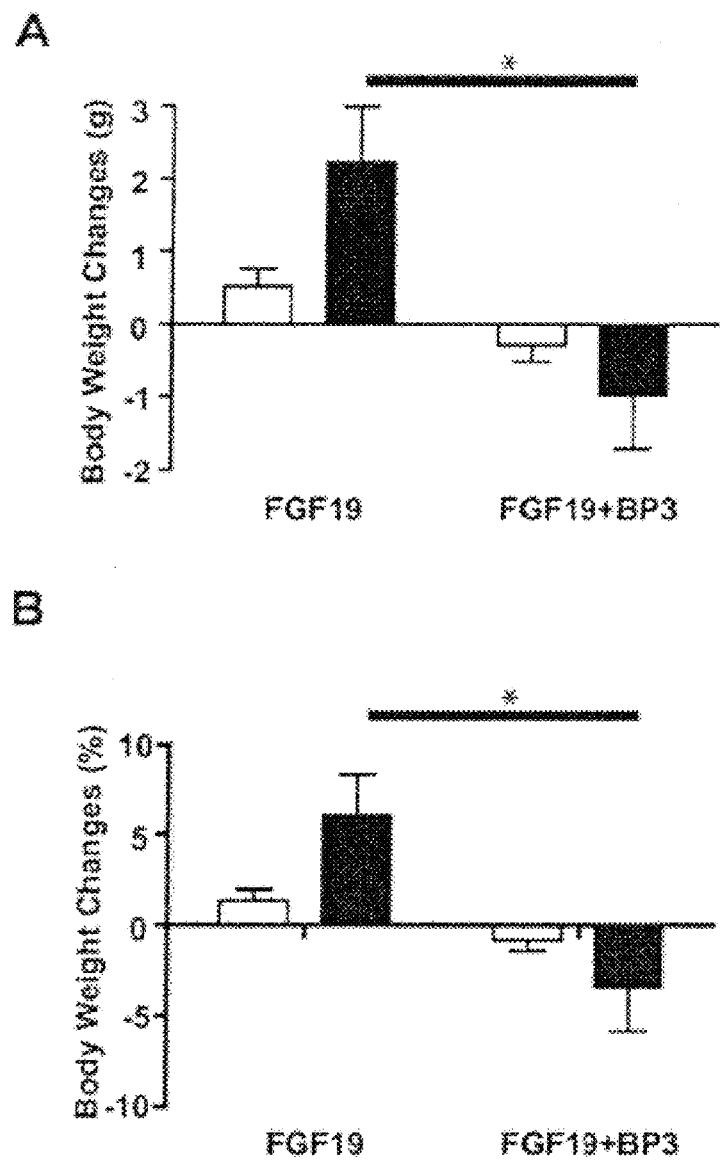
FIG. 11 depicts the body weight changes in ob/ob mice following single or multiple treatments with FGF19 or FGF19+BP3. A, The changes in body weight were significantly different between the FGF19 group and the combination group immediately after 5 treatments (2.2±0.8 g vs. −1.0±0.7 g), and a clear trend was also observed 2 days after a single treatment (p=0.055). Filled Squares: single treatment, Open Squares: 5 treatments at one dose/day. B, The percentage changes in body weight is also different between the two groups immediately after 5 daily treatments (6.04±2.33% vs.-3.40±2.50%). Filled Squares: single treatment; Open Squares: 5 treatments (one dose/day). * denotes P<0.05.

Two days after a single dose treatment with FGF19 (n=3) or FGF19+BP3 (n=5), ob/ob mice were weighed and the changes in body weight were compared between the two groups. No significant changes in body weight were found (FIG. 11A, 11B, 1 treatment) between the groups. However, 5 days of treatment (one dose/day) with FGF19+BP3 lowered the body weight by 1.0±0.7 g/animal, whereas 5 days of treatment (one dose/day) with FGF19 alone was associated with an increase in body weight (2.2±0.8 g/animal), which was similar to vehicle treated animals. For the 5 days of treatment, the changes in body weight were significantly different, in both grams and in percent body weight (p<0.05, FIG. 11A, 11B, 5 daily treatments).

BP3 enhances and prolongs the effects of FGF19 on glucose homeostasis, i.e., there is an improvement of the glucose tolerance, from either single or multiple doses. The combination of FGF19+BP3 also reduced the body weight per mouse after 1 dose/day for 5 days, while the animals in FGF19 treatment group gained weight. The combination of BP3 and FGF19 has an unexpectedly better therapeutic effect on obesity than FGF19 alone.

Given the proposed mechanism of action, it was surprising that a FGFBP3 enhanced the effects of FGF19, i.e., a molecule that that will not be retained by the extracellular matrix and that administration of a complex of FGF19 and FGFBP3 would affect metabolism more quickly, (i.e. after a single dose), for a longer period (i.e for up to two days after a single dose) and more profoundly (i.e. better efficacy in normalizing glucose tolerance) than FGF19 alone. These data support the concept that BP3+FGF19 treatment improves glucose metabolism in subjects with diabetes and that a single daily dose may be sufficient to last beyond 24 hours.

Figure 12:
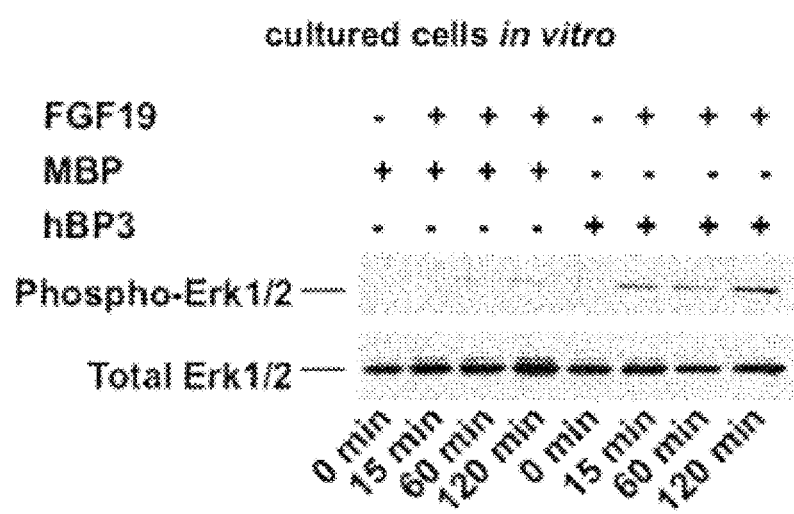
FIG. 12 depicts the presence of BP3 enhancing the ability of FGF19 to induce phosphorylation of Erk1/2 in HepG2 cells. HepG2 cells were treated with FGF19±BP3 or the negative control protein MBP. pERK1/2 was measured in cell lysates at different times after treatment.

To further explore a possible mechanism of action, HepG2 cells (hepatocellular carcinoma cells) were treated with FGF19 with or without BP3. FIG. 12 shows that the presence of BP3 enhanced the ability of FGF19 to induce phosphorylation of Erk1/2.

Example 5

Figure 13:
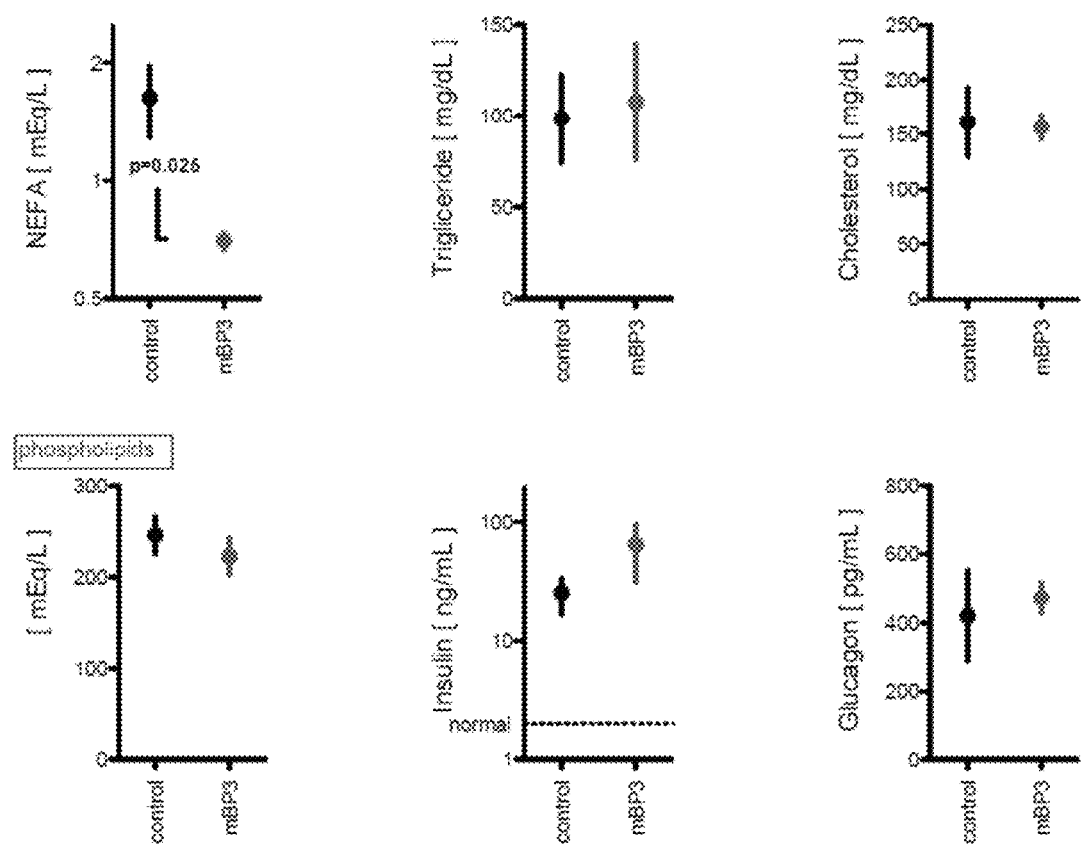
FIG. 13 depicts a significant reduction of non-esterified fatty acids (NEFA) in the serum (p=0.025) of transgenic animals expressing mouse FGFBP3. No significant changes in the other lipids were noted. In addition, the mice remained hyperinsulinemic, which is a known phenotype for ob/ob mice. FGFBP3 alone did not change glucagon or insulin levels significantly. The reduction of NEFA after BP3 expression indicates an improved metabolic disease state of the animals.

To understand the longterm effect, FGFBP3 was expressed in ob/ob, leptin deficient mice that develop metabolic disease. For this experiment, mouse FGFBP3 was used to avoid immune rejection of a human protein. Exogenously introduced FGFBP3 expression was achieved by injecting mice twice weekly with a liposomally packaged FGFBP3 expression plasmid to achieve uptake and expression of the exogenously introduce FGFBP3 gene. After 2½ weeks of treatments the content of blood in mice was analyzed as shown in FIG. 13.

What is claimed is:

1. A method of lowering blood glucose levels in a subject in need thereof, the method comprising administering fibroblast growth factor binding protein 3 (FGFBP3) to the subject in need of lowering blood glucose levels.

2. The method of claim 1, wherein the subject has diabetes.

3. The method of claim 1, wherein the subject is obese.

4. The method of claim 1, wherein subject is hyperglycemic.

5. The method of claim 1, wherein the subject has abnormal glycogen metabolism.

6. The method of claim 1, wherein the FGFBP3 is administered as a complex with fibroblast growth factor 19 (FGF19).

7. The method of claim 6, wherein the subject has diabetes.

8. The method of claim 6, wherein the subject is obese.

9. The method of claim 6, wherein the subject is hyperglycemic.

10. The method of claim 6, wherein the subject has abnormal glycogen metabolism.

11. A method of treating diabetes in a subject in need of treatment thereof, the method comprising administering fibroblast growth factor binding protein 3 (FGFBP3) to the subject in need of treatment of diabetes.

12. The method of claim 11, wherein the FGFBP3 is administered as a complex with fibroblast growth factor 19 (FGF19).

13. A method of treating hyperglycemia in a subject in need of treatment thereof, the method comprising administering fibroblast growth factor binding protein 3 (FGFBP3) to the subject in need of treatment of hyperglucemia.

14. The method of claim 13, wherein the FGFBP3 is administered as a complex with fibroblast growth factor 19 (FGF19).

15. The method any of claims 1-5 or 6-14, wherein hepatic triglyceride levels are not affected in the subject.

* * * * *

UNITED STATES PATENT AND TRADEMARK OFFICE
CERTIFICATE OF CORRECTION

| | |
|---|---|
| PATENT NO. | : 9,789,160 B2 |
| APPLICATION NO. | : 14/853482 |
| DATED | : October 17, 2017 |
| INVENTOR(S) | : Anton Wellstein |

It is certified that error appears in the above-identified patent and that said Letters Patent is hereby corrected as shown below:

In the Specification

At Column 1, Lines 6-10, delete the following paragraph:
"Part of the work performed during development of this invention utilized U.S. Government funds through National Institutes of Health Grant Nos. RO1 CA71508 and PO1 HL068686. The U.S. Government has certain rights in this invention."

And insert in its place the following paragraph:
--This invention was made with government support under grant numbers CA071508 and HL068686 awarded by the National Institutes of Health. The government has certain rights in the invention.--

Signed and Sealed this
Twelfth Day of December, 2023

Katherine Kelly Vidal
*Director of the United States Patent and Trademark Office*

SEQUENCE LISTING

```
<160> NUMBER OF SEQ ID NOS: 20

<210> SEQ ID NO 1
<211> LENGTH: 258
<212> TYPE: PRT
<213> ORGANISM: Artificial Sequence
<220> FEATURE:
<223> OTHER INFORMATION: Synthetic peptide - full length FGFBP3

<400> SEQUENCE: 1

Met Thr Pro Pro Lys Leu Arg Ala Ser Leu Ser Pro Ser Leu Leu Leu
1               5                   10                  15

Leu Leu Ser Gly Cys Leu Leu Ala Ala Ala Arg Arg Glu Lys Gly Ala
                20                  25                  30

Ala Ser Asn Val Ala Glu Pro Val Pro Gly Pro Thr Gly Gly Ser Ser
            35                  40                  45

Gly Arg Phe Leu Ser Pro Glu Gln His Ala Cys Ser Trp Gln Leu Leu
        50                  55                  60

Leu Pro Ala Pro Glu Ala Ala Gly Ser Glu Leu Ala Leu Arg Cys
65                  70                  75                  80

Gln Ser Pro Asp Gly Ala Arg His Gln Cys Ala Tyr Arg Gly His Pro
                85                  90                  95

Glu Arg Cys Ala Ala Tyr Ala Ala Arg Arg Ala His Phe Trp Lys Gln
            100                 105                 110

Val Leu Gly Gly Leu Arg Lys Lys Arg Arg Pro Cys His Asp Pro Ala
        115                 120                 125

Pro Leu Gln Ala Arg Leu Cys Ala Gly Lys Lys Gly His Gly Ala Glu
```

```
                  130                 135                 140
Leu Arg Leu Val Pro Arg Ala Ser Pro Pro Ala Arg Pro Thr Val Ala
145                 150                 155                 160

Gly Phe Ala Gly Glu Ser Lys Pro Arg Ala Arg Asn Arg Gly Arg Thr
                165                 170                 175

Arg Glu Arg Ala Ser Gly Pro Ala Ala Gly Thr Pro Pro Pro Gln Ser
            180                 185                 190

Ala Pro Pro Lys Glu Asn Pro Ser Glu Arg Lys Thr Asn Glu Gly Lys
                195                 200                 205

Arg Lys Ala Ala Leu Val Pro Asn Glu Glu Arg Pro Met Gly Thr Gly
210                 215                 220

Pro Asp Pro Asp Gly Leu Asp Gly Asn Ala Glu Leu Thr Glu Thr Tyr
225                 230                 235                 240

Cys Ala Glu Lys Trp His Ser Leu Cys Asn Phe Phe Val Asn Phe Trp
                245                 250                 255

Asn Gly

<210> SEQ ID NO 2
<211> LENGTH: 232
<212> TYPE: PRT
<213> ORGANISM: Artificial Sequence
<220> FEATURE:
<223> OTHER INFORMATION: Synthetic peptide - full length FGFBP3 without
      the signal sequence

<400> SEQUENCE: 2

Arg Arg Glu Lys Gly Ala Ala Ser Asn Val Ala Glu Pro Val Pro Gly
1               5                   10                  15

Pro Thr Gly Gly Ser Ser Gly Arg Phe Leu Ser Pro Glu Gln His Ala
                20                  25                  30

Cys Ser Trp Gln Leu Leu Pro Ala Pro Glu Ala Ala Ala Gly Ser
            35                  40                  45

Glu Leu Ala Leu Arg Cys Gln Ser Pro Asp Gly Ala Arg His Gln Cys
50                  55                  60

Ala Tyr Arg Gly His Pro Glu Arg Cys Ala Ala Tyr Ala Ala Arg Arg
65                  70                  75                  80

Ala His Phe Trp Lys Gln Val Leu Gly Gly Leu Arg Lys Lys Arg Arg
                85                  90                  95

Pro Cys His Asp Pro Ala Pro Leu Gln Ala Arg Leu Cys Ala Gly Lys
                100                 105                 110

Lys Gly His Gly Ala Glu Leu Arg Leu Val Pro Arg Ala Ser Pro Pro
            115                 120                 125

Ala Arg Pro Thr Val Ala Gly Phe Ala Gly Glu Ser Lys Pro Arg Ala
            130                 135                 140

Arg Asn Arg Gly Arg Thr Arg Glu Arg Ala Ser Gly Pro Ala Ala Gly
145                 150                 155                 160

Thr Pro Pro Pro Gln Ser Ala Pro Pro Lys Glu Asn Pro Ser Glu Arg
                165                 170                 175

Lys Thr Asn Glu Gly Lys Arg Lys Ala Ala Leu Val Pro Asn Glu Glu
                180                 185                 190

Arg Pro Met Gly Thr Gly Pro Asp Pro Asp Gly Leu Asp Gly Asn Ala
            195                 200                 205

Glu Leu Thr Glu Thr Tyr Cys Ala Glu Lys Trp His Ser Leu Cys Asn
210                 215                 220

Phe Phe Val Asn Phe Trp Asn Gly
```

```
225                 230

<210> SEQ ID NO 3
<211> LENGTH: 29
<212> TYPE: PRT
<213> ORGANISM: Artificial Sequence
<220> FEATURE:
<223> OTHER INFORMATION: Synthetic peptide - C-terminal FGFBP3

<400> SEQUENCE: 3

Leu Asp Gly Asn Ala Glu Leu Thr Glu Thr Tyr Cys Ala Glu Lys Trp
1               5                   10                  15

His Ser Leu Cys Asn Phe Phe Val Asn Phe Trp Asn Gly
            20                  25

<210> SEQ ID NO 4
<211> LENGTH: 66
<212> TYPE: PRT
<213> ORGANISM: Artificial Sequence
<220> FEATURE:
<223> OTHER INFORMATION: Synthetic peptide - C-terminal FGFBP3 "C66"
      peptide

<400> SEQUENCE: 4

Ala Pro Pro Lys Glu Asn Pro Ser Glu Arg Lys Thr Asn Glu Gly Lys
1               5                   10                  15

Arg Lys Ala Ala Leu Val Pro Asn Glu Glu Arg Pro Met Gly Thr Gly
            20                  25                  30

Pro Asp Pro Asp Gly Leu Asp Gly Asn Ala Glu Leu Thr Glu Thr Tyr
        35                  40                  45

Cys Ala Glu Lys Trp His Ser Leu Cys Asn Phe Phe Val Asn Phe Trp
    50                  55                  60

Asn Gly
65

<210> SEQ ID NO 5
<211> LENGTH: 36
<212> TYPE: PRT
<213> ORGANISM: Artificial Sequence
<220> FEATURE:
<223> OTHER INFORMATION: Synthetic peptide - Tat protein basic peptide
      motif 37-72

<400> SEQUENCE: 5

Cys Phe Ile Thr Lys Ala Leu Gly Ile Ser Tyr Gly Arg Lys Lys Arg
1               5                   10                  15

Arg Gln Arg Arg Arg Pro Pro Gln Gly Ser Gln Thr His Gln Val Ser
            20                  25                  30

Leu Ser Lys Gln
        35

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide - Tat protein residues 48-57

<400> SEQUENCE: 6

Gly Arg Lys Lys Arg Arg Gln Arg Arg Arg
1               5                   10

<210> SEQ ID NO 7
```

```
<211> LENGTH: 23
<212> TYPE: DNA
<213> ORGANISM: Artificial Sequence
<220> FEATURE:
<223> OTHER INFORMATION: PCR Primer

<400> SEQUENCE: 7
ggcgcttttg actcaggatt taa                                               23

<210> SEQ ID NO 8
<211> LENGTH: 24
<212> TYPE: DNA
<213> ORGANISM: Artificial Sequence
<220> FEATURE:
<223> OTHER INFORMATION: PCR Primer

<400> SEQUENCE: 8
cctcagccac atttgtagaa cttt                                              24

<210> SEQ ID NO 9
<211> LENGTH: 26
<212> TYPE: DNA
<213> ORGANISM: Artificial Sequence
<220> FEATURE:
<223> OTHER INFORMATION: PCR Primer

<400> SEQUENCE: 9
cccacagtta atgcacttgg atcctg                                            26

<210> SEQ ID NO 10
<211> LENGTH: 30
<212> TYPE: DNA
<213> ORGANISM: Artificial Sequence
<220> FEATURE:
<223> OTHER INFORMATION: PCR Primer

<400> SEQUENCE: 10
gggcatgtag aaatacttca gcttgtttcc                                        30

<210> SEQ ID NO 11
<211> LENGTH: 24
<212> TYPE: DNA
<213> ORGANISM: Artificial Sequence
<220> FEATURE:
<223> OTHER INFORMATION: PCR Primer

<400> SEQUENCE: 11
tctttgtcgg aagactgtca acgg                                              24

<210> SEQ ID NO 12
<211> LENGTH: 26
<212> TYPE: DNA
<213> ORGANISM: Artificial Sequence
<220> FEATURE:
<223> OTHER INFORMATION: PCR Primer

<400> SEQUENCE: 12
catcatactg atccaggaac tcccga                                            26

<210> SEQ ID NO 13
<211> LENGTH: 27
<212> TYPE: DNA
<213> ORGANISM: Artificial Sequence
<220> FEATURE:
<223> OTHER INFORMATION: PCR Primer

<400> SEQUENCE: 13
```
gtcactttga gatctactcg gcaaacc    27

<210> SEQ ID NO 14
<211> LENGTH: 24
<212> TYPE: DNA
<213> ORGANISM: Artificial Sequence
<220> FEATURE:
<223> OTHER INFORMATION: PCR Primer

<400> SEQUENCE: 14
tctgaccaca gtgaggaatg tcca    24

<210> SEQ ID NO 15
<211> LENGTH: 21
<212> TYPE: DNA
<213> ORGANISM: Artificial Sequence
<220> FEATURE:
<223> OTHER INFORMATION: PCR Primer

<400> SEQUENCE: 15
cgactcgcta tctccaagtg a    21

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16
gttgaaccag tctccgacca    20

<210> SEQ ID NO 17
<211> LENGTH: 21
<212> TYPE: DNA
<213> ORGANISM: Artificial Sequence
<220> FEATURE:
<223> OTHER INFORMATION: PCR Primer

<400> SEQUENCE: 17
tcctgtaaaa gcccggagta t    21

<210> SEQ ID NO 18
<211> LENGTH: 19
<212> TYPE: DNA
<213> ORGANISM: Artificial Sequence
<220> FEATURE:
<223> OTHER INFORMATION: PCR Primer

<400> SEQUENCE: 18
gctctggtag gggcagtga    19

<210> SEQ ID NO 19
<211> LENGTH: 19
<212> TYPE: DNA
<213> ORGANISM: Artificial Sequence
<220> FEATURE:
<223> OTHER INFORMATION: PCR Primer

<400> SEQUENCE: 19
accgacttgg tcagcgaag    19

<210> SEQ ID NO 20
<211> LENGTH: 20
<212> TYPE: DNA

```
<213> ORGANISM: Artificial Sequence
<220> FEATURE:
<223> OTHER INFORMATION: PCR Primer

<400> SEQUENCE: 20
cacgagcccg tagttgtcat                                              20
```